US011642408B2

United States Patent
Nam et al.

(10) Patent No.: US 11,642,408 B2
(45) Date of Patent: May 9, 2023

(54) ANTIGEN VARIANT OF VARICELLA ZOSTER VIRUS AND USE THEREOF

(71) Applicant: MOGAM INSTITUTE FOR BIOMEDICAL RESEARCH, Yongin-si (KR)

(72) Inventors: Hyo Jung Nam, Yongin-si (KR); Ga Young Ji, Yongin-si (KR); Eunmi Kim, Yongin-si (KR)

(73) Assignee: MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 84 days.

(21) Appl. No.: 17/057,378

(22) PCT Filed: May 22, 2019

(86) PCT No.: PCT/KR2019/006113
§ 371 (c)(1),
(2) Date: Nov. 20, 2020

(87) PCT Pub. No.: WO2019/225962
PCT Pub. Date: Nov. 28, 2019

(65) Prior Publication Data
US 2021/0187099 A1 Jun. 24, 2021

(30) Foreign Application Priority Data
May 23, 2018 (KR) ........................ 10-2018-0058219

(51) Int. Cl.
*A61K 39/25* (2006.01)
*A61P 31/22* (2006.01)
*C07K 14/005* (2006.01)
*C12N 7/00* (2006.01)

(52) U.S. Cl.
CPC ............. *A61K 39/25* (2013.01); *A61P 31/22* (2018.01); *C07K 14/005* (2013.01); *C12N 7/00* (2013.01); *C12N 2710/16722* (2013.01); *C12N 2710/16734* (2013.01); *C12N 2710/16771* (2013.01)

(58) Field of Classification Search
CPC ............ A61K 39/25; A61K 2039/5254; A61K 2039/545; A61K 39/12; A61P 31/22; C07K 14/005; C12N 7/00; C12N 2710/16722; C12N 2710/16734; C12N 2710/16771; C12N 2710/16022; C12N 2710/16034
See application file for complete search history.

(56) References Cited

U.S. PATENT DOCUMENTS

| 5,824,319 | A | 10/1998 | Vafai |
| 7,939,084 | B1 | 5/2011 | Hanon et al. |
| 2006/0121052 | A1* | 6/2006 | Sotelo-Morales ..... A61K 39/12 424/199.1 |
| 2011/0104260 | A1* | 5/2011 | Hanon .................... A61P 37/04 424/450 |
| 2014/0023673 | A1* | 1/2014 | Weiner .................... C12N 7/00 435/320.1 |
| 2018/0372745 | A1 | 12/2018 | Suzuki et al. |

FOREIGN PATENT DOCUMENTS

| CN | 102517302 A | * | 6/2012 |
| CN | 102517302 A | | 6/2012 |
| KR | 10-2014-0006115 A | | 1/2014 |
| WO | 2006/094756 A2 | | 9/2006 |
| WO | 2006/128026 A2 | | 11/2006 |
| WO | 2017/090744 A1 | | 6/2017 |

OTHER PUBLICATIONS

Li Q, Ali MA, Cohen JI. Insulin degrading enzyme is a cellular receptor mediating varicella-zoster virus infection and cell-to-cell spread. Cell. Oct. 20, 2006;127(2):305-16. (Year: 2006).*
Otto RB, Burkin K, Amir SE, Crane DT, Bolgiano B. Patterns of binding of aluminum-containing adjuvants to Haemophilus influenzae type b and meningococcal group C conjugate vaccines and components. Biologicals. Sep. 2015;43(5):355-62. Epub Jul. 17, 2015. (Year: 2015).*
Loparev VN. Membrane glycoprotein gE [Human alphaherpesvirus 3], GenBank: ABH08489.1. Dep. Jun. 30, 2007. (Year: 2007).*
Lal H, Cunningham AL, Godeaux O, Chlibek R, Diez-Domingo J, Hwang SJ, Levin MJ, McElhaney JE, Poder A, Puig-Barberà J, et. al; ZOE-50 Study Group. Efficacy of an adjuvanted herpes zoster subunit vaccine in older adults. N Engl J Med. May 28, 2015;372(22):2087-96. Epub Apr. 28, 2015. (Year: 2015).*
Thomsson E, Persson L, Grahn A, Snäil J, Ekblad M, Brunhage E, Svensson F, Jern C, Hansson GC, Bäckström M, Bergström T. Recombinant glycoprotein E produced in mammalian cells in large-scale as an antigen for varicella-zoster-virus serology. J Virol Methods. Jul. 2011;175(1):53-9. Epub Apr. 22, 2011. (Year: 2011).*
Lindblad EB, Schønberg NE. Aluminum adjuvants: preparation, application, dosage, and formulation with antigen. Methods Mol Biol. 2010;626:41-58. doi: 10.1007/978-1-60761-585-9_4. PMID: 20099120. (Year: 2010).*

(Continued)

*Primary Examiner* — Rachel B Gill
(74) *Attorney, Agent, or Firm* — Sughrue Mion, PLLC

(57) ABSTRACT

An antigen variant and a use thereof are disclosed. The antigen variant is a protein, among surface proteins (gE) of the varicella zoster virus, exhibits a high expression level and high immunogenicity, and thus, when the antigen variant is used as a vaccine composition, the vaccine composition has more excellent safety compared to a live virus vaccine, and the antigen variant exhibits a higher expression level in a host cell compared to other antigens. The antigen variant is useful as a vaccine for preventing or treating chicken pox or herpes zoster caused by the varicella zoster virus.

12 Claims, 6 Drawing Sheets
Specification includes a Sequence Listing.

(56) References Cited

OTHER PUBLICATIONS

Adriana Weinberg, et al., "Varicella-Zoster Virus-Specific Immune Responses to Herpes Zoster in Elderly Participants in a Trial of a Clinically Effective Zoster Vaccine", The Journal of Infectious Diseases, Oct. 1, 2009, pp. 1068-1077, vol. 200, No. 7.

Judith Breuer, et al., "Varicella and herpes zoster vaccine development: lessons learned", Expert Review of Vaccines, DOI:10.1080/14760584.2017.1394843, 2017, 33 pages.

Jonas Schmidt-Chanasit, et al., Novel Varicella-Zoster Virus Glycoprotein E Gene Mutations Associated with Genotypes A and D, Journal of Clinical Microbiology, Jan. 2008, pp. 325-327, vol. 46, No. 1.

Jennifer Moffat, et al., "Functions of the C-Terminal Domain of Varicella-Zoster Virus Glycoprotein E in Viral Replication In Vitro and Skin and T-Cell Tropism In Vivo", Journal of Virology, Nov. 2004, pp. 12406-12415, vol. 78, No. 22.

NCBI, GenBank accession No. NP_040190.1, Feb. 2015.

International Search Report for PCT/KR2019/006113 dated Aug. 20, 2019 (PCT/ISA/210).

Hiroshi Kimura et al., "Baculovirus Expression, Purification, and Properties of Varicella-Zoster Virus gE,gI,and the Complex They Form", Journal of Infectious Diseases, 1998, vol. 178, Suppl. 1, pp. s13-s15 (3 pages total).

"Committee for Medicinal Products for Human Use (CHMP) Assessment report of SHINGRIX", European Medicines Agency, Jan. 25, 2018, XP055489835, pp. 1-170 (173 pages total).

Michele Haumont et al., "Purification, characterization and immunogenicity of recombinant varicella-zoster virus glycoprotein gE secreted by Chinese hamster ovary cells", Virus Research, 1996, vol. 40, No. 2, pp. 199-204 (6 pages total).

\* cited by examiner

FIG. 2

ANTIGEN VARIANT OF VARICELLA ZOSTER VIRUS AND USE THEREOF

CROSS REFERENCE TO RELATED APPLICATIONS

This application is a National Stage of International Application No. PCT/KR2019/006113 filed May 22, 2019, claiming priority based on Korean Patent Application No. 10-2018-0058219 filed May 23, 2018.

TECHNICAL FIELD

The present invention relates to a Varicella Zoster Virus antigen variant and a use thereof, and more particularly to a Varicella Zoster Virus antigen variant having high expression level and high immunogenicity, which is selected among Varicella Zoster Virus surface protein (gE) antigen variants, and a vaccine composition for preventing or treating varicella or herpes zoster which comprises the Varicella Zoster Virus antigen variant as an active ingredient.

BACKGROUND ART

Varicella Zoster Virus (VZV) is a virus that causes varicella mainly in children and adolescents. Once infection occurs, VZV remains dormant in sensory root and cranial nerve ganglion cells for several years, and is reactivated and causes herpes zoster in adulthood when immunity decreases. Varicella is highly contagious; and once infection occurs, it causes a blister-like rash all over the body with fever and malaise. In most normal children, varicella rarely progresses to a serious condition and eventually progress to a self-limited disease. However, it is known that many cases where varicella progresses to serious symptoms occur in patients who have undergone organ transplantation or chemotherapy (Adriana Weinberg et al., J Infectious Diseases, 200(7): 1068, 2009; Judith Breuer et al., Expert Review of Vaccines, 2017, DOI:10.1080/14760584.2017.1394843).

Herpes zoster has initial symptoms of aches and pains all over the body like body aches, or sensations of severe itching, tingling, and burning, with severe pain like being stabbed with a knife. Herpes zoster is a disease in which blisters develop after a few days, pain increases as skin lesions increase, and older patients tend to complain of more severe pain. Even in a case where Herpes zoster is cured, it may leave neuralgia as a sequela. It is known that in people aged 60 or higher, the neuralgia may cause them to sleep fitfully, cause them to complain of chronic fatigue, cause them to feel severe pain even upon light contact or friction, or cause even depression, although such neuralgia is relatively rare in adults aged 40 or lower.

Representative preventive vaccines against varicella include products such as VARIVAX™ (Merck & Co, Inc.) and VARILRIX™ (GlaxoSmithKline Biologicals SA), which were developed using Oka strain, an attenuated strain developed in 1970. In Korea, a product such as SUDUVAX™ (Green Cross), which was produced using MAV/06 strain developed in 1980, is commercially available. The commercially available live vaccines in question show an average of 80% protective efficacy, which means that infection occurs in 20% of vaccinees even after vaccination. Stability problems have been constantly pointed out, such as occurrence of varicella and herpes zoster caused by live viruses contained in the vaccines.

ZOSTAVAX™ (Merck & Co, Inc.), which is a live attenuated vaccine produced using Oka strain, was developed as a preventive vaccine against herpes zoster. This vaccine has been approved and sold in the US and Korea under a condition that it should be used for adults aged 50 or higher, not for children or adolescents, due to the fact that a large amount of virus is contained in the vaccine. Recently, a vaccine composed of a viral surface protein (gE) and an adjuvant, which is intended for adults aged 50 or higher, was developed by GlaxoSmithKline Biologicals SA, and proved to have preventive efficacy in clinical trials (U.S. Pat. No. 7,939,084, issued on Jan. 7, 2011).

In the early stages of vaccine development, live attenuated cells or dead cells were mainly used as antigens. However, due to safety issues and immunosuppressive substances present in pathogens, development of such antigens is shifting to development of protein antigens which have a clear structure and composition and can establish immunity essential for disease defense.

Accordingly, the present inventors have made intensive efforts to develop protein antigens with a high expression level in host cells, which can contribute to productivity improvement without affecting immunogenicity, out of Varicella Zoster Virus surface protein (gE) antigens. As a result, the prevent inventors have produced Varicella Zoster Virus surface protein antigen variants of various lengths and measured expression levels thereof, thereby identifying specific amino acid sequences with a high expression level, among the antigen variants; and thus have completed the present invention.

DISCLOSURE OF INVENTION

Technical Problem

An object of the present invention is to provide a specific antigen variant having high expression level and high immunogenicity, which is selected among Varicella Zoster Virus surface protein (gE) antigen variants.

Another object of the present invention is to provide a gene encoding the antigen variant, a recombinant vector comprising the gene, and a host cell transformed with the recombinant vector.

Yet another object of the present invention is to provide a vaccine composition for preventing or treating varicella or herpes zoster, comprising the antigen variant as an active ingredient.

Still yet another object of the present invention is to provide a method for preventing or treating varicella or herpes zoster, using a vaccine composition that comprises the antigen variant as an active ingredient.

Still yet another object of the present invention is to provide a use of a vaccine composition that comprises the antigen variant as an active ingredient, for prevention or treatment of varicella or herpes zoster.

Still yet another object of the present invention is to provide a use of a vaccine composition that comprises the antigen variant as an active ingredient, for manufacture of a medicament for preventing or treating varicella or herpes zoster.

Solution to Problem

To achieve the above objects, in the present invention, there is provided a Varicella Zoster Virus surface protein antigen variant which is characterized in that the antigen variant includes a variation which is truncation of the carboxy terminus of any one amino acid residue selected from the group consisting of the $525^{th}$ to $543^{rd}$ amino acid residues in the Varicella Zoster Virus surface protein (gE) antigen represented by the amino acid sequence of SEQ ID NO: 1.

In addition, in the present invention, there are provided a gene encoding the antigen variant, a recombinant vector comprising the gene, and a host cell transformed with the recombinant vector.

In addition, in the present invention, there is provided a vaccine composition for preventing or treating varicella or herpes zoster, comprising the antigen variant as an active ingredient.

In addition, in the present invention, there is provided a method for preventing or treating varicella or herpes zoster, using a vaccine composition that comprises the antigen variant as an active ingredient.

In addition, in the present invention, there is provided a use of a vaccine composition that comprises the antigen variant as an active ingredient, for prevention or treatment of varicella or herpes zoster.

In addition, in the present invention, there is provided a use of a vaccine composition that comprises the antigen variant as an active ingredient, for manufacture of a medicament for preventing or treating varicella or herpes zoster.

BRIEF DESCRIPTION OF DRAWINGS

FIG. 2 illustrates amino acid sequences of Varicella Zoster Virus surface protein (gE) antigens of various lengths. In FIG. 2, VZV gE antigen variant gE 500 aa has the sequence of SEQ ID NO: 16, gE 505 aa has the sequence of SEQ ID NO: 17, gE 510 aa has the sequence of SEQ ID NO: 18, gE 515 aa has the sequence of SEQ ID NO: 19, gE 520 aa has the sequence of SEQ ID NO: 20, gE 525 aa has the sequence of SEQ ID NO: 21, gE 530 aa has the sequence of SEQ ID NO: 22, gE 534 aa has the sequence of SEQ ID NO: 2, gE 537 aa has the sequence of SEQ ID NO: 5, gE 540 aa has the sequence of SEQ ID NO: 8, gE 543 aa has the sequence of SEQ ID NO: 23, and gE 546 aa has the sequence of SEQ ID NO: 24.

BEST MODE FOR CARRYING OUT THE INVENTION

Unless defined otherwise, all technical and scientific terms used herein have the same meaning as commonly understood by those skilled in the art to which the present invention pertains. In general, the nomenclature used herein is well known and commonly used in the art.

Figure 1:
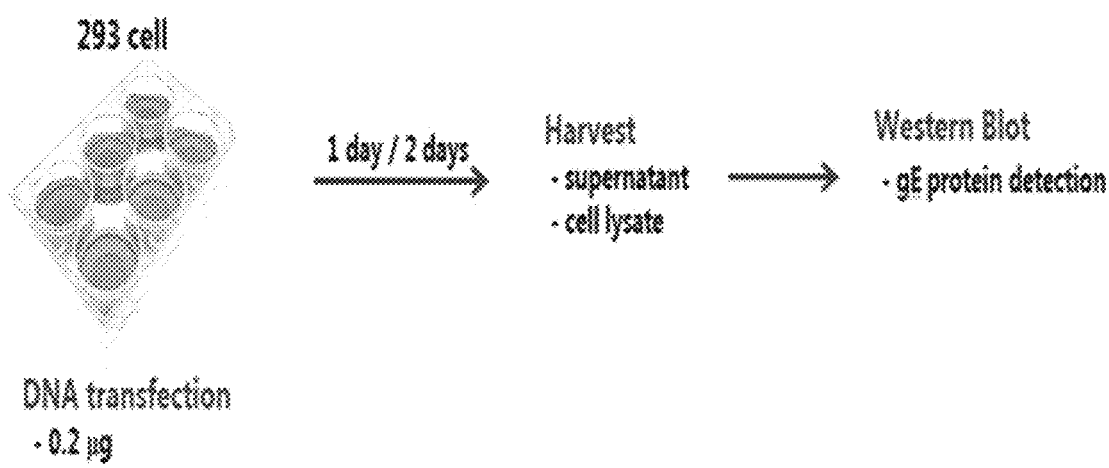
FIG. 1 schematically illustrates an experimental process according to the present invention.
Figure 3:
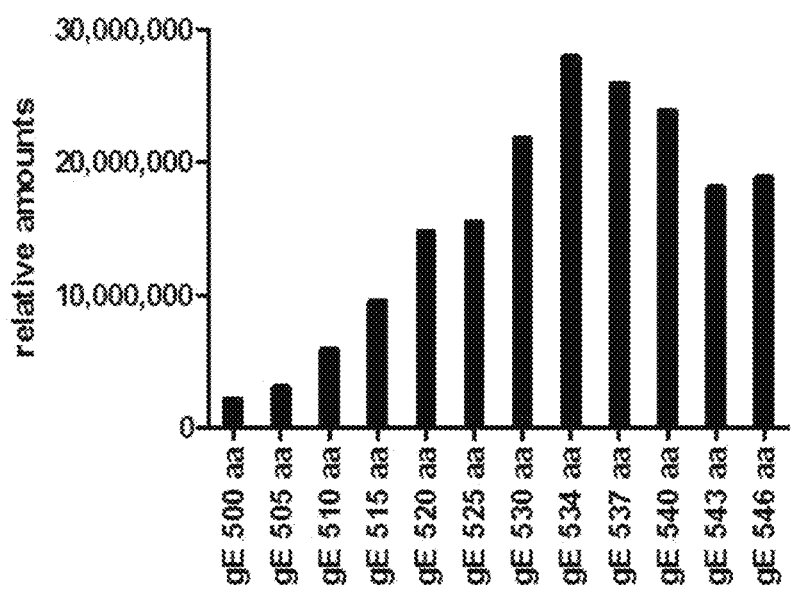
FIG. 3 illustrates results of Western blot performed to compare expression levels of gE fragments that are Varicella Zoster Virus antigens.

In the present invention, to develop antigens with a high expression level in host cells, which can contribute to productivity improvement without affecting immunogenicity, out of Varicella Zoster Virus protein antigens, an experiment was performed, in which surface protein (gE) antigen variants of various lengths are produced and then expression levels thereof are measured. As a result, it was identified that among the Varicella Zoster Virus surface protein antigen variants produced by the present inventors, antigens represented by specific amino acid sequences exhibited a higher expression level than the other antigens (FIG. 3).

In addition, antibody titer measurement (FIG. 7) and antigen-specific responder measurement (FIG. 8) were performed to select antigen variants having high immunogenicity. As a result, it was identified that mogam gE 534 aa to gE 540 aa had higher immunogenicity.

Therefore, in an aspect of the present invention, there is provided a Varicella Zoster Virus surface protein antigen variant which is includes a variation which is truncation of the carboxy terminus of any one amino acid residue selected from the group consisting of the $525^{th}$ to $543^{rd}$ amino acid residues in the Varicella Zoster Virus surface protein (gE) antigen represented by the amino acid sequence of SEQ ID NO: 1.

Specifically, in the present invention, there is provided a Varicella Zoster Virus surface protein antigen variant which is characterized in that the antigen variant includes a variation selected from the group consisting of:

a) truncation of the carboxy terminus of the $525^{th}$ amino acid residue;

b) truncation of the carboxy terminus of the $526^{th}$ amino acid residue;

c) truncation of the carboxy terminus of the $527^{th}$ amino acid residue;

d) truncation of the carboxy terminus of the $528^{th}$ amino acid residue;

e) truncation of the carboxy terminus of the $529^{th}$ amino acid residue;

f) truncation of the carboxy terminus of the $530^{th}$ amino acid residue;

g) truncation of the carboxy terminus of the $531^{th}$ amino acid residue;

h) truncation of the carboxy terminus of the $532^{nd}$ amino acid residue;

i) truncation of the carboxy terminus of the $533^{rd}$ amino acid residue;

j) truncation of the carboxy terminus of the $534^{th}$ amino acid residue;

k) truncation of the carboxy terminus of the $535^{th}$ amino acid residue;

l) truncation of the carboxy terminus of the $536^{th}$ amino acid residue;

m) truncation of the carboxy terminus of the 537$^{th}$ amino acid residue;

n) truncation of the carboxy terminus of the 538$^{th}$ amino acid residue;

o) truncation of the carboxy terminus of the 539$^{th}$ amino acid residue;

p) truncation of the carboxy terminus of the 540$^{th}$ amino acid residue;

q) truncation of the carboxy terminus of the 541$^{st}$ amino acid residue;

r) truncation of the carboxy terminus of the 542$^{nd}$ amino acid residue; and s) truncation of the carboxy terminus of the 543$^{rd}$ amino acid residue.

The antigenic variant may be characterized in that it preferably includes a variation selected from the group consisting of j) truncation of the carboxy terminus of the 534$^{th}$ amino acid residue; k) truncation of the carboxy terminus of the 535$^{th}$ amino acid residue; l) truncation of the carboxy terminus of the 536$^{th}$ amino acid residue; m) truncation of the carboxy terminus of the 537$^{th}$ amino acid residue; n) truncation of the carboxy terminus of the 538$^{th}$ amino acid residue; o) truncation of the carboxy terminus of the 539$^{th}$ amino acid residue; and p) truncation of the carboxy terminus of the 540$^{th}$ amino acid residue; however, the variation is not limited thereto.

SEQ ID NO: 1: mgtvnkpvvg vlmgfgiitg tlritnpvra svlryddfhX$_1$ dedkldtnsv yepyyhsdha esswvnrges srkaydhnsp yiwprndydg flenahehhg vynqgrgids gerlmqptqm saqedlgddt gihviptlng ddrhkivnvd qrqygdvfkg dlnpkpqgqr lievsveenh pftlrapiqr iygvrytetw sflpsltctg daapaiqhic lkhttcfqdv vvdvdcaent kedqlaeisy rfqgkkeadq pwivvntstl fdeleldppe iepgvlkvlr tekqylgvyi wnmrgsdgts tyatflvtwk gdektrnptp avtpqprgae fhmwnyhshv fsvgdtfsla mhlqykihea pfdllewly vpidptcqpm rlystclyhp napqclshmn sgctftsphl aqrvastvyq ncehadnyta yclgishmep sfglilhdgg ttlkfvdtpe slsglyvfvv yfnghveava ytvvstvdhf vnaieergfp ptagqppatt kpkeitpvnp gtsplX$_2$ryaa wtgglaavvl lclviflict akrmrvkayr vdkspynqsm yyaglpvddf edsestdtee efgnaiggsh ggssytvyid ktr (wherein X$_1$ is T or I, and X$_2$ is L or I).

In the present invention, the Varicella Zoster Virus surface protein antigen variant may be characterized in that it is a Varicella Zoster Virus surface protein antigen variant consisting of 534 to 540 amino acids, which is derived from the Varicella Zoster Virus surface protein antigen represented by the amino acid sequence of SEQ ID NO: 1 consisting of 623 amino acids or a variation which is truncation of the carboxy terminus in some amino acid residues. For example, as used herein, the term "variation which is truncation of the carboxy terminus of the 534$^{th}$ amino acid residue" means that in the direction from amino terminus (N-terminus) to carboxy terminus (C-terminus), Pt to 534$^{th}$ amino acid residues remain and contiguous amino acid residues from the 535$^{th}$ amino acid residue to the carboxy terminus are truncated.

According to a specific embodiment of the present invention, the 40$^{th}$ amino acid residue in the amino acid sequence of SEQ ID NO: 1 is threonine.

According to a specific embodiment of the present invention, the 536$^{th}$ amino acid residue in the amino acid sequence of SEQ ID NO: 1 is leucine.

In the present invention, the Varicella Zoster Virus surface protein antigen variant may be characterized in that it is represented by any one amino acid sequence of SEQ ID NOs: 2 to 8 and SEQ ID NOs: 21 to 23, as follows:

a) an antigen variant represented by the amino acid sequence of SEQ ID NO: 2, which is obtained by truncation of the carboxy terminus of the 534$^{th}$ amino acid residue;

b) an antigen variant represented by the amino acid sequence of SEQ ID NO: 3, which is obtained by truncation of the carboxy terminus of the 535$^{th}$ amino acid residue;

c) an antigen variant represented by the amino acid sequence of SEQ ID NO: 4, which is obtained by truncation of the carboxy terminus of the 536$^{th}$ amino acid residue;

d) an antigen variant represented by the amino acid sequence of SEQ ID NO: 5, which is obtained by truncation of the carboxy terminus of the 537$^{th}$ amino acid residue;

e) an antigen variant represented by the amino acid sequence of SEQ ID NO: 6, which is obtained by truncation of the carboxy terminus of the 538$^{th}$ amino acid residue;

f) an antigen variant represented by the amino acid sequence of SEQ ID NO: 7, which is obtained by truncation of the carboxy terminus of the 539$^{th}$ amino acid residue;

g) an antigen variant represented by the amino acid sequence of SEQ ID NO: 8, which is obtained by truncation of the carboxy terminus of the 540$^{th}$ amino acid residue;

h) an antigen variant represented by the amino acid sequence of SEQ ID NO: 21, which is obtained by truncation of the carboxy terminus of the 525$^{th}$ amino acid residue;

i) an antigen variant represented by the amino acid sequence of SEQ ID NO: 22, which is obtained by truncation of the carboxy terminus of the 530$^{th}$ amino acid residue; or j) an antigen variant represented by the amino acid sequence of SEQ ID NO: 23, which is obtained by truncation of the carboxy terminus of the 543$^{rd}$ amino acid residue.

The surface protein of the present invention is derived from a glycoprotein constituting the envelope of Varicella Zoster Virus derived from Clade 1, and is a peptide fragment (truncated protein) consisting of 534 to 540 amino acids which is obtained by truncation of a part of the carboxy terminus.

Given biologically equivalent amino acid variations, the amino acid sequence used in the present invention is interpreted to include sequences having substantial identity with the sequences of SEQ ID NOs: 2 to 8 and SEQ ID NOs: 21 to 23. The above-mentioned substantial identity means that in a case where the sequence of the present invention as described above and any other sequence are aligned for maximum correspondence and the aligned sequences are analyzed using an algorithm commonly used in the art, the other sequence has at least 70% homology, more particularly 80% homology, even more particularly 90% homology, and most particularly 95% homology to the sequence of the present invention while having the same function.

In an embodiment of the present invention, it was identified that the following antigen variant has high immunogenicity: a) an antigen variant represented by the amino acid sequence of SEQ ID NO: 2, which is obtained by truncation of the carboxy terminus of the 534$^{th}$ amino acid residue; b) an antigen variant represented by the amino acid sequence of SEQ ID NO: 3, which is obtained by truncation of the carboxy terminus of the 535$^{th}$ amino acid residue; c) an antigen variant represented by the amino acid sequence of SEQ ID NO: 4, which is obtained by truncation of the carboxy terminus of the 536$^{th}$ amino acid residue; d) an antigen variant represented by the amino acid sequence of SEQ ID NO: 5, which is obtained by truncation of the carboxy terminus of the 537$^{th}$ amino acid residue; e) an antigen variant represented by the amino acid sequence of SEQ ID NO: 6, which is obtained by truncation of the carboxy terminus of the 538$^{th}$ amino acid residue; f) an antigen variant represented by the amino acid sequence of SEQ ID NO: 7, which is obtained by truncation of the carboxy terminus of the 539$^{th}$ amino acid residue; or g) an antigen variant represented by the amino acid sequence of SEQ ID NO: 8, which is obtained by truncation of the carboxy terminus of the 540$^{th}$ amino acid residue.

In the early stages of vaccine development, live attenuated cells or dead cells were mainly used as antigens. However, due to safety issues, development of such antigens is shifting to development of protein antigens which have a clear structure and composition. However, protein antigens are generally problematic in that they have low immunogenicity as compared with conventional vaccines. From the viewpoints of being excellent in both stability and immunogenicity and being expressed at a high level in host cells, the antigen variant according to the present invention can be effectively used as a vaccine for preventing or treating Varicella Zoster Virus-induced varicella or herpes zoster.

In another aspect of the present invention, there are provided a gene encoding the antigenic variant, a recombinant vector comprising the same, and a host cell transformed with the recombinant vector.

In the present invention, the gene may be characterized in that it is represented by any one nucleotide sequence of SEQ ID NOs: 9 to 15.

As used herein, the term "vector" refers to a DNA construct containing a DNA sequence that is operably linked to a suitable control sequence capable of effecting expression of the DNA sequence in a suitable host. The vector may be a plasmid, a phage particle, or simply a potential genomic insert. Once transformed into a suitable host, the vector may replicate and function independently of the host genome, or may, in some cases, integrate into the genome itself. In the present specification, "plasmid" and "vector" are sometimes used interchangeably as a plasmid is currently the most commonly used form of vector. For the purpose of the present invention, it is preferred to use a plasmid vector. Typical plasmid vectors, which can be used for this purpose, have a structure including (a) a replication origin that allows effective replication such that several hundred plasmid vectors per host cell are produced, (b) an antibiotic-resistant gene that allows selection of a host cell transformed with the plasmid vector, and (c) a restriction enzyme cleavage site that allows a foreign DNA fragment to be inserted. Even if an appropriate restriction enzyme cleavage site does not exist in a vector, using a synthetic oligonucleotide adapter or linker according to a conventional method enables easy ligation of the vector and foreign DNA.

As used herein, the term "recombinant vector" usually refers to a recombinant carrier into which a fragment of heterologous DNA is inserted, the recombinant carrier being generally in the form of a double-stranded DNA fragment. Here, the heterologous DNA refers to foreign DNA that is not naturally found in a host cell. The recombinant vector, once in a host cell, can replicate independently of the host chromosomal DNA so that several copies of the vector and (heterologous) DNA inserted therein can be produced.

After ligation, the gene or the recombinant vector is transformed or transfected into a host cell. For the "transformation" or "transfection", several types of various techniques commonly used to introduce an exogenous nucleic acid (DNA or RNA) into prokaryotic or eukaryotic host cells may be used, and examples thereof include electroporation, calcium phosphate precipitation, DEAE-dextran transfection, and lipofection.

As is well known in the art, to increase an expression level of a transfected gene in a host cell, the gene in question should be operably linked to a transcriptional and translational expression control sequence which exerts its function in a selected expression host.

As used herein, the term "transformation" refers to introduction of DNA into a host so that the DNA can be replicated as an extrachromosomal factor or by chromosomal integration. Of course, it should be understood that not all vectors function equally in expressing the gene sequence of the present invention. Likewise, not all hosts function equally with respect to the same expression system. However, those skilled in the art can make an appropriate selection among various vectors, expression control sequences, and hosts without departing from the scope of the present invention without undue experimental burden. For example, a vector must be selected in consideration of a host, because the vector must replicate therein. In this regard, a copy number of the vector, its ability to regulate the copy number, and expression of other proteins encoded by the vector must also be considered.

In the present invention, the host cell to be transformed is preferably selected from, but not limited to, the group consisting of animal cells, plant cells, yeast, *E. coli*, and insect cells.

Specifically, in the present invention, as the microorganism used as the host cell to be transformed, any microorganism may be used as long as it is a non-toxic or attenuated microorganism when applied to a living body. Examples thereof may include Gram negative bacteria such as *E. coli, Salmonella typhi, Salmonella typhimurium, Vibrio cholerae, Mycobacterium bovis*, and *Shigella*; and Gram positive bacteria such as *Bacillus, Lactobacillus, Lactococcus, Staphylococcus, Listeria monocytogenes*, and *Streptococcus*. A preferred example thereof may include lactic acid bacteria that are edible microorganisms. However, the microorganism is not limited thereto.

The lactic acid bacteria may include *Lactobacillus* sp., *Streptococcus* sp., and *Bifidobacterium* sp. Representative examples of *Lactobacillus* sp. may include *Lactobacillus acidophilus, Lactobacillus plantarum, Lactobacillus fermentum, Lactobacillus delbrueckii, Lactobacillus johnsonii, Lactobacillus reuteri, Lactobacillus bulgaricus*, and *Lactobacillus casei*; representative examples of *Streptococcus* sp. may include *Streptococcus* thermophiles; and representative examples of *Bifidobacterium* sp. may include *Bifidobacterium infantis, Bifidobacterium bifidum, Bifidobacterium longum, Bifidobacterium breve, Bifidobacterium lactis*, and *Bifidobacterium adolescentis*, with *Lactobacillus casei* being more preferred. However, the lactic acid bacteria are not limited thereto.

The microorganism may also be eukaryotic cells, including fungi such as *Aspergillus* sp., yeast such as *Pichia pastoris, Saccharomyces cerevisiae, Schizosaccharomyces* sp., and *Neurospora crassa*, other lower eukaryotic cells, and higher eukaryotic cells such as cells from insects.

The microorganism may be derived from plants or mammals. Preferred examples thereof may include monkey kidney cells (COS-7 cells), NS0 cells, SP2/0, Chinese hamster ovary (CHO) cells, W138, baby hamster kidney (BHK) cells, MDCK, myeloma cell lines, HuT78 cells, and HEK293 cells, with CHO cells being preferred. However, the microorganism is not limited thereto.

In yet another aspect of the present invention, there is provided a method for producing a Varicella Zoster Virus antigen, comprising a step of culturing the host cell.

In a case where a recombinant vector capable of expressing the Varicella Zoster Virus antigen is introduced into a host cell, the antigen may be produced by culturing the host cell for a period sufficient to allow the antigen to be expressed therein, or more preferably, for a period sufficient to allow the antigen to be secreted into culture medium in which the host cell is cultured.

In some cases, the expressed antigen may be isolated from the host cell and purified to homogeneity. Isolation or purification of the antigen may be performed by conventional isolation and purification methods used for proteins, for example, chromatography. Examples of the chromatography may include affinity chromatography including Protein A column or Protein G column, ion exchange chromatography, and hydrophobic chromatography. The antigen may be isolated and purified by further combining filtration, ultrafiltration, salting-out, dialysis, and the like, in addition to the above chromatography.

In still yet another aspect of the present invention, there is provided a vaccine composition for preventing or treating varicella or herpes zoster, comprising, as an active ingredient, the Varicella Zoster Virus antigen variant.

In still yet another aspect of the present invention, there is provided a method for preventing or treating varicella or herpes zoster, using a vaccine composition that comprises, as an active ingredient, the Varicella Zoster Virus antigen variant.

In still yet another aspect of the present invention, there is provided a use of a vaccine composition that comprises, as an active ingredient, the Varicella Zoster Virus antigen variant, for prevention or treatment of varicella or herpes zoster.

In still yet another aspect of the present invention, there is provided a use of a vaccine composition that comprises, as an active ingredient, the antigen variant, for manufacture of a medicament for preventing or treating varicella or herpes zoster.

As used herein, the term "prevention" means inhibiting occurrence of a condition or disease in a subject who has not been diagnosed as having the condition or disease and is likely to have such a condition or disease.

As used herein, the term "treatment" means (a) inhibiting progress of a condition or disease, or symptoms thereof; (b) alleviating a condition or disease, or symptoms thereof; or (c) eliminating a condition or disease, or symptoms thereof. The composition of the present invention activates an immune response against Varicella Zoster Virus in an individual suffering from varicella or herpes zoster, which is a disease caused by Varicella Zoster Virus infection, thereby functioning to inhibit progress of, eliminate, or alleviate symptoms of the disease. Accordingly, the composition of the present invention may itself be a therapeutic composition for varicella or herpes zoster, or may be applied as a therapeutic aid for the disease which is administered in combination with other pharmacological ingredients.

Thus, in the present specification, the term "treatment" or "therapeutic agent" also includes the meaning of "adjuvant treatment" or "treatment aid".

As used herein, the term "active ingredient" refers to a vaccine composition sufficient to produce a desired effect which includes, but is not limited to, inducing or increasing an immune response against Varicella Zoster Virus in a patient, preventing, alleviating, or eliminating reactivation of Varicella Zoster Virus in a patient infected with the same virus or administered a live Varicella Zoster Virus vaccine, preventing herpes zoster (HZ) and/or post-herpetic neuralgia (PHN), and decreasing severity or duration of HZ and/or PHN. Those skilled in the art appreciate that a level of such a desired effect may vary.

As used herein, the term "immune response" refers to a cell-mediated (T-cell) immune response and/or an antibody (B-cell) response.

The vaccine composition of the present invention is useful for preventing varicella and/or HZ and/or PHN, or decreasing severity or duration of varicella and/or HZ and/or PHN, in populations of immunocompetent and immunocompromised patients which include, but are not limited to, healthy individuals and immunocompromised patients who have undergone hematopoietic cell transplantation (HCT) or solid organ transplantation (SOT), HIV-infected patients, patients with an autoimmune disease, and individuals with blood cancer; individuals who undergo chemotherapy for a wide variety of solid malignancies; and patients who undergo chronic immunosuppressive therapy for a wide variety of conditions, including rheumatoid arthritis (RA), systemic lupus erythematosus (SLE), Crohn's disease, psoriasis, and multiple sclerosis.

In the present invention, the vaccine composition may be characterized in that it further comprises a pharmaceutically acceptable carrier, excipient, or diluent.

The vaccine composition of the present invention may be prepared in a unit dosage form by being formulated using a pharmaceutically acceptable carrier and/or excipient according to a method that can be easily carried out by a person skilled in the art to which the present invention pertains, or may be prepared in a form of being placed in a multi-dose container. Here, the dosage form may be formulated in the form of oral preparations such as powders, granules, tablets, capsules, suspensions, emulsions, syrups, and aerosols, preparations for external use, suppositories, and sterile injectable solutions according to conventional methods, and used. Suitable formulations known in the art may be those disclosed in Remington's Pharmaceutical Science, Mack Publishing Company, Easton Pa.

Solid preparations for oral administration include tablets, pills, powders, granules, capsules, and the like, and these solid preparations are prepared by being mixed with at least one excipient such as starch, calcium carbonate, sucrose, lactose, and gelatin. In addition to simple excipients, lubricants such as magnesium stearate and talc are also used for the solid preparations.

Liquid preparations for oral administration include suspensions, oral liquids, emulsions, syrups, and the like, and these liquid preparations may contain various excipients such as wetting agents, sweetening agents, fragrances, and preservatives, in addition to water and liquid paraffin which are commonly used simple diluents.

Preparations for parenteral administration include sterile aqueous solutions, non-aqueous solvents, suspensions, emulsions, lyophilized preparations, and suppositories. As a base for suppositories, WITEPSOL™, MACROGOL™, TWEEN™ 61, cacao fat, laurinum, glycerogelatin, and the like may be used.

In the present invention, the vaccine composition may be characterized in that it further comprises an adjuvant. In general, an immune response is not strongly induced by a protein antigen alone, and thus an effect of the vaccine composition is increased by being mixed with the adjuvant.

As used herein, the term "adjuvant" refers to a substance that non-specifically promotes an immune response to an antigen in an initial activation process of immune cells, including an agent, a molecule, and the like, each of which is not an immunogen to a host and enhances immunity by increasing activity of cells in the immune system (Warren et al., Annu. Rev. Immunol, 4:369, 1986). The adjuvant used in the present invention, which can potentiate an immune response, may be administered simultaneously with the vaccine composition or may be sequentially administered at a time interval.

The adjuvant of the present invention may be characterized in that it is selected from, but not limited to, the group consisting of calcium phosphate hydroxide, mineral oil, squalene, toll-like receptor (TLR) antagonist, detergent, liposome, saponin, cytokine, and combinations thereof.

In still yet another aspect of the present invention, there is provided a method for treating or preventing a disease or disorder in a patient, comprising a step of administering, to the patient, a therapeutically effective amount of the vaccine composition.

An optimal dose of the vaccine composition of the present invention can be determined by standard studies involving observation of a suitable immune response in a subject. After initial vaccination, the subject may be subjected to one or several booster immunizations at appropriate intervals.

A suitable dose of the vaccine composition of the present invention varies depending on factors such as formulation method, mode of administration, the patient's age, weight, sex, pathological condition, diet, time of administration, route of administration, excretion rate, and response sensitivity, and may be appropriately determined by those skilled in the art in consideration of the above-mentioned factors.

The vaccine composition of the present invention may be administered through a route commonly used in the field of medicine. Parenteral administration is preferred, and the administration may be, for example, made through intravenous, intraperitoneal, intramuscular, intraarterial, oral, intracardiac, intramedullary, intradural, transdermal, intestinal, subcutaneous, sublingual, or topical route. In general, the vaccine composition of the present invention may be characterized in that it comprises, as an active ingredient, the Varicella Zoster Virus surface protein antigen variant according to the present invention in a therapeutically effective amount.

MODE FOR THE INVENTION

Hereinafter, the present invention will be described in more detail by way of examples. These examples are for illustrative purposes only, and it will be apparent to those of ordinary skill in the art that the scope of the present invention is not construed as being limited by these examples.

Example 1: Production of Surface Protein (gE) Constructs

To produce surface protein (gE) constructs, PCR was performed to obtain desired gE fragments. Then, each of the gE fragments was cleaved with a restriction enzyme and inserted into pcDNA3.1 vector. A sequence of the gE fragment inserted into the pcDNA3.1 vector was identified through sequencing. DNA of the pcDNA3.1 vector comprising the sequence-identified gE fragment was obtained by midiprep. Amino acid sequences of the surface protein (gE) fragments are shown in Table 1 below.

TABLE 1

| VZV gE antigen variant | Variation in VZV gE antigen of SEQ ID NO: 1 | SEQ ID NO: |
|---|---|---|
| gE 534 aa | Truncation of carboxy terminus of 534$^{th}$ amino acid residue | 2 |
| gE 535 aa | Truncation of carboxy terminus of 535$^{th}$ amino acid residue | 3 |
| gE 536 aa | Truncation of carboxy terminus of 536$^{th}$ amino acid residue | 4 |
| gE 537 aa | Truncation of carboxy terminus of 537$^{th}$ amino acid residue | 5 |
| gE 538 aa | Truncation of carboxy terminus of 538$^{th}$ amino acid residue | 6 |
| gE 539 aa | Truncation of carboxy terminus of 539$^{th}$ amino acid residue | 7 |
| gE 540 aa | Truncation of carboxy terminus of 540$^{th}$ amino acid residue | 8 |
| gE 500 aa | Truncation of carboxy terminus of 500$^{th}$ amino acid residue | 16 |
| gE 505 aa | Truncation of carboxy terminus of 505$^{th}$ amino acid residue | 17 |
| gE 510 aa | Truncation of carboxy terminus of 510$^{th}$ amino acid residue | 18 |
| gE 515 aa | Truncation of carboxy terminus of 515$^{th}$ amino acid residue | 19 |
| gE 520 aa | Truncation of carboxy terminus of 520$^{th}$ amino acid residue | 20 |
| gE 525 aa | Truncation of carboxy terminus of 525$^{th}$ amino acid residue | 21 |
| gE 530 aa | Truncation of carboxy terminus of 530$^{th}$ amino acid residue | 22 |
| gE 543 aa | Truncation of carboxy terminus of 543$^{rd}$ amino acid residue | 23 |
| gE 546 aa | Truncation of carboxy terminus of 546$^{th}$ amino acid residue | 24 |

Example 2: Transient Transfection

To identify expression levels of the gE fragments, transient transfection thereof into 293 cells was performed using LIPOFECTAMINE™ 3000. $5 \times 10^5$ cells were added to each well of 6-well plate and culture was performed. Then, the following day, samples were prepared for transfection. 0.2 μg of DNA and 0.4 μg of P3000 were added to a tube and then diluted with 125 μL of OPTIMEM™; and 3.75 μL of LIPOFECTAMINE™ 3000 was added to another tube and then diluted with 125 μL of OPTIMEM™. The diluted DNA was transferred to the tube with an equal amount of the diluted LIPOFECTAMINE™ 3000. Then, the tube was incubated with mixing at room temperature for 10 minutes to prepare a DNA-LIPOFECTAMINE™ mix. After completion of the incubation, the DNA-LIPOFECTAMINE™ mix was added to the 293 cell-containing 6-well plate, and then culture was performed in a $CO_2$ incubator for 2 days. After completion of the culture, a supernatant was obtained, 4× sample buffer containing b-mercaptoethanol was added thereto, and then heating was performed at 100° C. for 5 minutes. After heating, the resultant was kept frozen until Western blot was performed.

Example 3: Western Blot

Western blot was performed to compare expression levels of the gE fragments. Each sample was run on NUPAGE™ 4-12% Bis-Tris Gel, and then transferred to a PVDF membrane. The membrane was blocked for 1 hour in 5% skim milk, incubated with monoclonal gE antibody (1 μg/mL) for 2 hours, washed with TBST (Tween 0.05%), and then incubated for 1 hour with goat anti-mouse IgG-HRP diluted 5000×. The incubated membrane was washed with TBST and then developed with ECL substrate. Detection was performed with a Chemidoc machine. As a result of performing Western blot, as illustrated in FIG. 3, it was found that the antigens, gE 534 aa, gE 537 aa, and gE 540 aa, exhibited a higher expression level.

Figure 4:
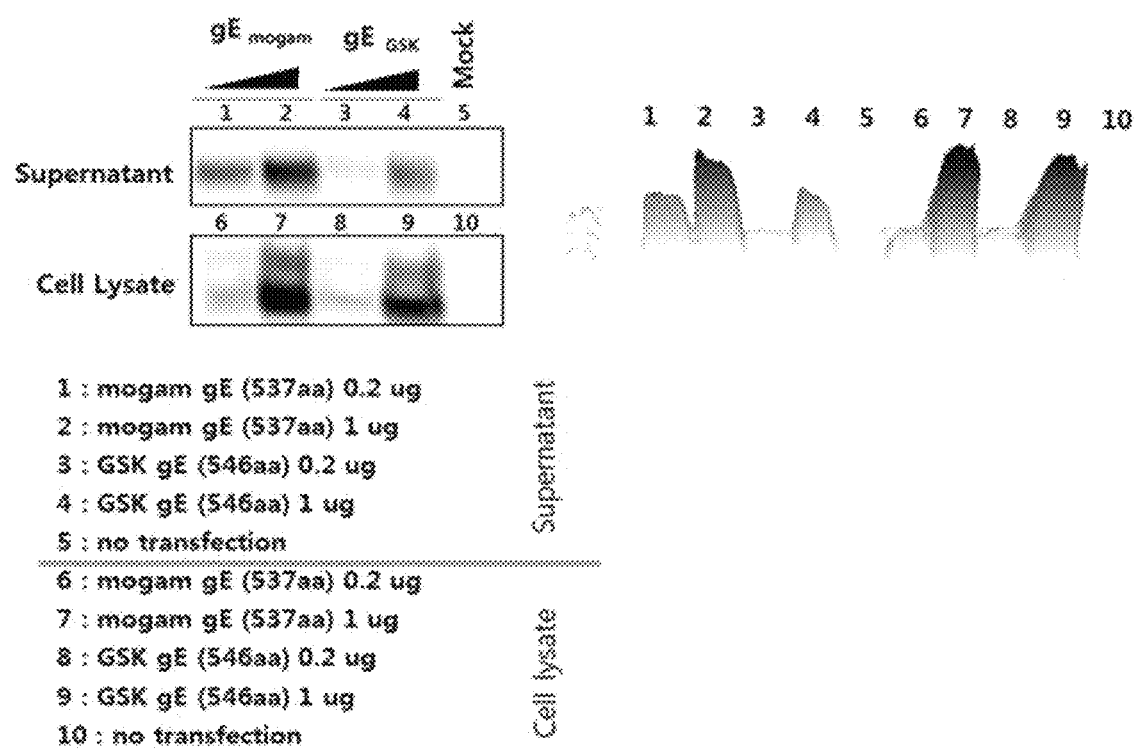
FIG. 4 illustrates results of Western blot performed to compare expression levels of a surface protein antigen (GSK gE 546 aa), which is contained in SHINGRIX® that is a Varicella Zoster Virus vaccine manufactured by GlaxoSmithKline Biologicals SA, and an antigen variant (mogam gE 537 aa) produced by the present inventors.

Example 4: Comparison, in Terms of Expression Level, with Varicella Zoster Virus Surface Protein Antigen of GlaxoSmithKline Biologicals SA To compare, in terms of expression level, a surface protein antigen (GSK gE 546 aa) contained in SHINGRIX™, which is a currently commercialized Varicella Zoster Virus vaccine of GlaxoSmithKline Biologicals SA, and an antigen (mogam gE 537 aa) produced by the present inventors, Western blot was performed in the same manner as described in Example 3. Differences between the surface protein antigen (GSK gE 546 aa) contained in SHINGRIX™ of GlaxoSmithKline Biologicals SA and the antigen (mogam gE 537 aa) produced by the present inventors are as shown in Table 2 below. As a result of performing Western blot, as illustrated in FIG. 4, it was found that the antigen produced by the present inventors exhibited a higher expression level than the surface protein antigen of GlaxoSmithKline Biologicals SA.

TABLE 2

|  | mogam gE 537 aa | GSK gE 546 aa |
|---|---|---|
| Source | Clade 1 | Clade 3 |
|  | (wild type, strain Dumas) | (wild type) |
| 40$^{th}$ amino acid | T | I |
| 536$^{th}$ amino acid | L | I |
| C-terminal | w/o YAAWTGGLA | YAAWTGGLA |
|  | (SEQ ID NO: 25) | (SEQ ID NO: 25) |

Example 5: Comparison, in Terms of Immunogenicity, with Varicella Zoster Virus Surface Protein Antigen of GlaxoSmithKline Biologicals SA To compare, in terms of immunogenicity, a surface protein antigen (GSK gE 546 aa) contained in SHINGRIX™, which is a currently commercialized Varicella Zoster Virus vaccine of GlaxoSmithKline Biologicals SA, and an antigen (mogam gE 537 aa) produced by the present inventors, an animal experiment was carried out. From the viewpoint that humans have a history of varicella infection, to mimic varicella infection in mice, female C57BL/6 mice were subjected to primary immunization (LAV priming) by being subcutaneously injected once with a live attenuated vaccine (LAV. 3,000 pfu). After 28 days from the LAV priming (Day 0), the mice were subjected to secondary immunization by being intramuscularly injected with a mogam gE or GSK gE antigen composition with or without an adjuvant. Blood samples were collected 42 days (Day 42) after the LAV priming to measure a humoral immune response to gE; and leukocytes were collected from spleen samples 42 days (Day 42) after the LAV priming to measure a cell-mediated immune response (CMI) to gE or VZV. The day of immunization, and the day of collecting blood and spleen samples were calculated from the LAV priming day which was taken as Day 0. The overall animal experimental method is as described in Table 3 below.

TABLE 3

| Group | Primary immunization (LAV priming*) | Secondary immunization | | Day of secondary immunization | Day of collecting blood and spleen samples |
|---|---|---|---|---|---|
| | | Antigen | Adjuvant | | |
| PBS | PBS-only | X | X | Day 28 | Day 42 |
| LAV | LAV | LAV (15,000 Pfu) | X | | |
| gE (GSK) | LAV | gE (5 μg) | X | | |
| gE (mogam) | LAV | gE (5 μg) | X | | |
| gE (GSK) + adjuvant A | LAV | gE (5 μg) | Adjuvant A | | |
| gE (mogam) + adjuvant A | LAV | gE (5 μg) | Adjuvant A | | |

*Primary immunization (LAV priming): dose of 100 μL/head. 3,000 pfu
*Secondary immunization: dose of 100 μL/head

Example 5-1: Comparison of Humoral Immune Responses

Figure 5:
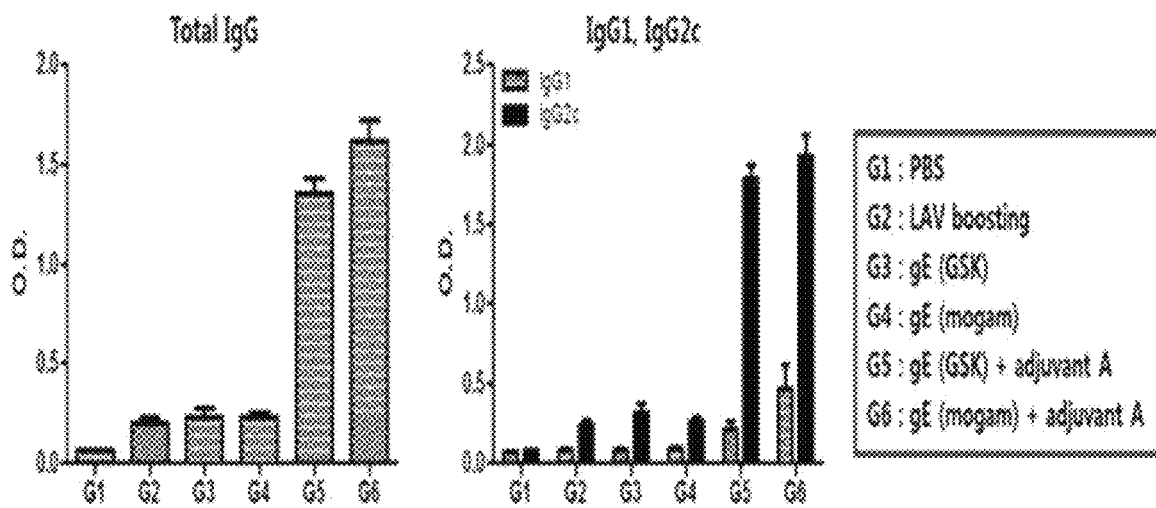
FIG. 5 illustrates results of anti-gE specific IgG ELISA performed to compare humoral immune responses of a surface protein antigen (GSK gE 546 aa), which is contained in SHINGRIX® that is a Varicella Zoster Virus vaccine manufactured by GlaxoSmithKline Biologicals SA, and an antigen variant (mogam gE 537 aa) produced by the present inventors.

After performing the primary and secondary immunizations, enzyme-linked immunosorbent assay (ELISA) was performed to measure gE antigen-specific IgG potency. Recombinant gE proteins (1 μg/mL) were dispensed onto ELISA plates, and overnight incubation was performed at 4° C. to allow the protein antigens to be coated thereon. Each of the antigen-coated ELISA plates was washed three times, and then blocked with a phosphate-buffered saline (PBS) solution containing 2% bovine serum albumin (BSA) for 1 hour. After completion of the blocking reaction with BSA, the ELISA plate was washed. Then, a diluted serum sample was added thereto and incubation was performed for 2 hours. Horseradish peroxidase (HRP)-conjugated goat anti-mouse IgG, IgG1, or IgG2c antibody was added thereto and incubation was performed for 1 hour. After the final incubation, the ELISA plate was washed, and HRP reaction was induced by addition of 3,3',5,5'-tetramethylbenzidine (TMB, manufactured by KPL) which is an HRP substrate. Then, TMB stop solution was added to stop the HRP reaction, and optical density (OD) was measured at 450 nm using an ELISA microplate reader (SPECTRAMAX™ 250, Molecular Device) to check an amount of antibody produced. As a result, as illustrated in FIG. 5, it was shown that G6 containing the antigen (mogam gE 537 aa) produced by the present inventors and an adjuvant had the highest luminescence intensity. From these results, it was found that the highest humoral immune response was induced in G6.

Example 5-2: Comparison of Cell-Mediated Immune Responses

Figure 6:
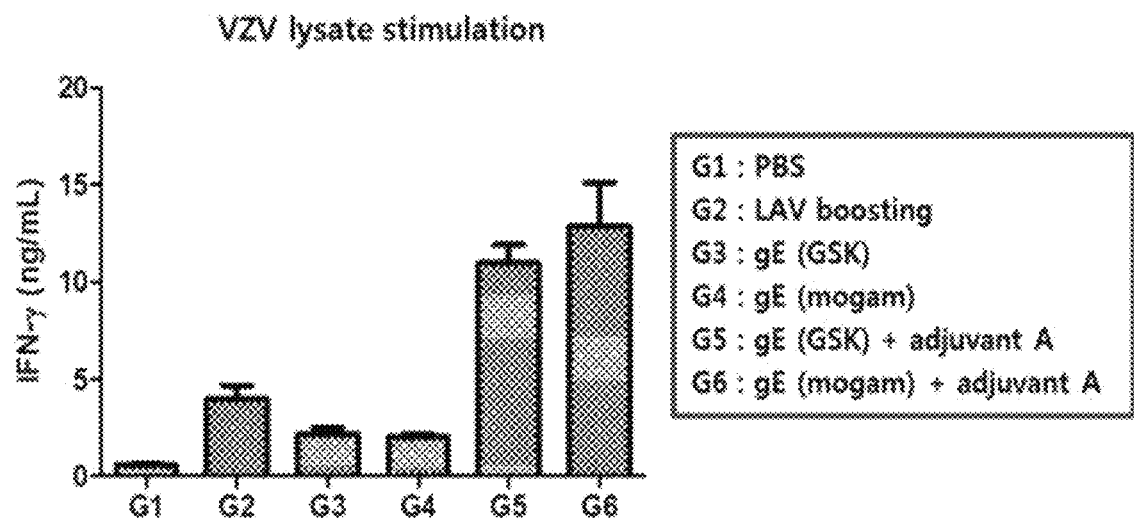
FIG. 6 illustrates results of mouse IFN-γ ELISA performed to compare cell-mediated immune responses (CMI) of a surface protein antigen (GSK gE 546 aa), which is contained in SHINGRIX® that is a Varicella Zoster Virus vaccine manufactured by GlaxoSmithKline Biologicals SA, and an antigen variant (mogam gE 537 aa) produced by the present inventors.

After performing the primary and secondary immunizations, IFN-γ ELISA was performed to check a secreted amount of IFN-γ, which is a representative cytokine secreted by T cells upon antigen stimulation. Leukocytes collected from mice were stimulated with VZV lysate for 3 days. Then, centrifugation was performed to obtain a supernatant, and the supernatant was analyzed with a mouse IFN-γ ELISA kit. IFN-γ capture antibody (4 μg/mL) was dispensed onto ELISA plates, and overnight incubation was performed at room temperature to allow the IFN-γ capture antibody to be coated thereon. Each of the antibody-coated ELISA plates was washed three times, and then blocked with PBS containing 1% bovine serum albumin (BSA) for 1 hour. After completion of the blocking reaction with BSA, the ELISA plate was washed. Then, the supernatant obtained after stimulation of the leukocytes was added thereto and incubation was performed at room temperature for 2 hours. After completion of the incubation, the ELISA plate was washed and incubation with biotinylated mouse IFN-γ detection antibody (400 ng/mL) was performed at room temperature for 2 hours. Washing was performed, and then incubation with streptavidin-HRP was performed for another 20 minutes. The finally incubated ELISA plate was washed, and then reacted with a substrate solution for 20 minutes at room temperature. A stop solution was added thereto to stop the reaction, and then optical density (OD) was measured at 450 nm using an ELISA microplate reader (SPECTRAMAX™ 250, Molecular Device) to check an amount of IFN-γ cytokine produced. As a result, as illustrated in FIG. 6, it was shown that G6 containing the antigen (mogam gE 537 aa) produced by the present inventors and an adjuvant exhibited the largest amount of IFN-γ cytokine. From these results, it was found that the highest cell-mediated immune response was induced in G6.

Example 6: Identification of Antigen-Specific Immunogenicity of gE Antigen Fragments Example 6-1: Transient Transfection for Antigen Production To express the gE fragments, transient transfection thereof into 293 cells was performed using the EXPI-FECTAMINE™ 293 transfection kit. The cells at $2 \times 10^6$ cells/mL were placed in a 125 mL flask and cultured. Then, the following day, transfection was performed. The 293 cells were diluted to a total of 25.5 mL at $2.9 \times 10^6$ cells/mL, and complexes for transfection were prepared. 30 μg of DNA was taken in a 15 mL tube and adjusted to 1.5 mL using OPTI-MEM™. In this way, Complex 1 was prepared. 81 μL of EXPIFECTAMINE™ 293 Reagent was placed in another 15 mL tube and adjusted to 1.5 mL using OPTI-MEM™. In this way, Complex 2 was prepared. Incubation was performed at room temperature for 5 minutes. After 5 minutes, Complex 1 was transferred to the Complex 2-containing tube and mixing was performed. Then, the tube was incubated at room temperature for 20 minutes to prepare a DNA-lipid complex. After completion of the incubation, the DNA-lipid complex was all placed in the 293 cell-containing 125 mL flask, and culture was performed in an incubator. 20 hours later, treatment with Enhancers was performed. 150 μL of EXPIFECTAMINE™ 293 Transfection Enhancer 1 was placed in a 1.5 mL tube, and EXPIFECTAMINE™ 293 Transfection Enhancer 2 was added thereto to 1.5 mL. Then, the resultant was added to the 293 cells and incubation was performed in an incubator for 5 days. After 5 days, the culture supernatant was obtained, filtered through a 0.45 μm filter, and stored frozen until purification.

Example 6-2: Purification to Obtain Antigens

The culture solution, which had been stored frozen, was thawed, and an equal amount of PBS was added to the culture solution. Filtration was performed using a 0.22 μm filter, and then Anion Exchange Chromatography was performed. To the eluate was added 5M NaCl, and Hydrophobic Interaction Chromatography was performed. The eluate that had undergone the chromatography was filtered through a 0.22 μm filter and stored frozen until animal experiments were performed.

Example 6-3: Immunization

Animal experiments were performed to identify immunogenicity of the gE antigen fragments. Female C57BL/6 mice were intramuscularly injected with the gE antigen fragments at a 2-week interval, and blood samples were collected from the mice 2 weeks after the secondary immunization. Sera were separated from the collected blood samples, and then stored frozen until antibody titer was measured.

Example 6-4: Measurement of Antigen-Specific IgG Potency and Responders

Enzyme-linked immunosorbent assay (ELISA) was performed to measure antigen-specific IgG potency. VZV surface proteins (1 μg/mL) were coated on ELISA plates, overnight incubation was performed at 4° C., and each of the ELISA plates was washed 3 times. Then, the ELISA plate was blocked with a phosphate-buffered saline (PBS) solution containing 2% bovine serum albumin (BSA) for 1 hour. The ELISA plate was washed. Then, a diluted serum sample was added thereto and incubation was performed for 2 hours. Horseradish peroxidase (HRP)-conjugated goat anti-mouse IgG antibody was added thereto and incubation was performed for 1 hour. After the final incubation, the ELISA plate was washed, and HRP reaction was induced by addition of 3,3',5,5'-tetramethylbenzidine (TMB) which is a substrate. Then, ELISA stop solution was added thereto to stop the HRP reaction, and optical density (OD) was measured using a spectrometer at 450 nm.

Figure 7:
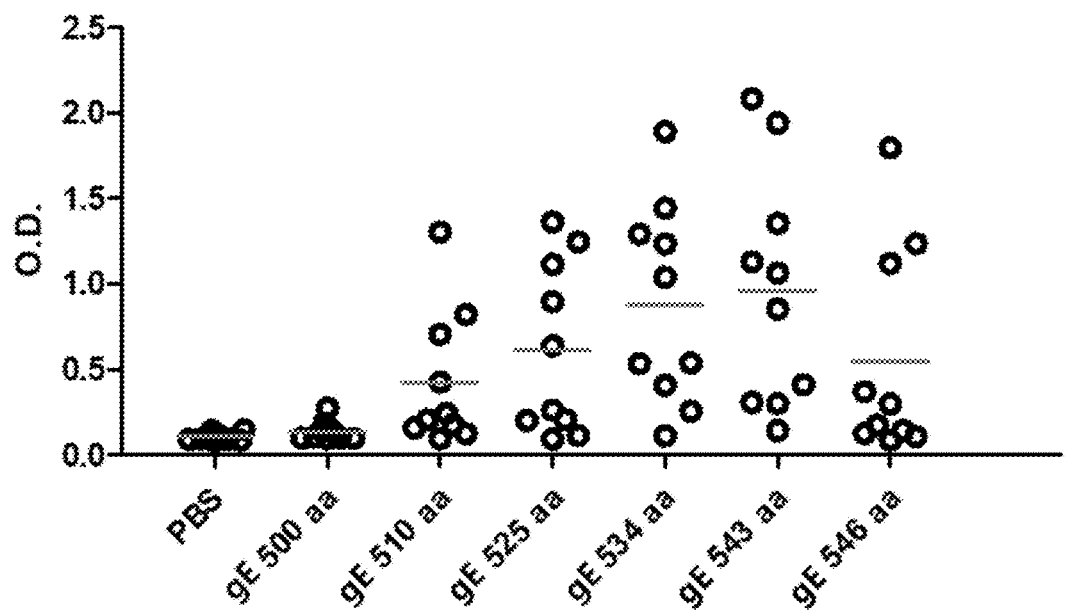
FIG. 7 illustrates results of anti-gE specific IgG ELISA performed to compare humoral immune responses of gE fragments that are Varicella Zoster Virus antigens.

To identify whether a difference in sequence between the gE antigen fragments causes a difference in antigen-specific immunogenicity, animal immunization was performed by the method as described in Example 6-3. Antigen-specific antibody titer was measured using sera obtained in the animal experiments according to the above antibody titer measurement method. As a result, as illustrated in FIG. 7, the OD value after immunization with gE 534 aa or gE 543 aa was higher than the OD value after immunization with gE 500 aa, gE 510 aa, gE 525 aa, or gE 546 aa.

Figure 8:
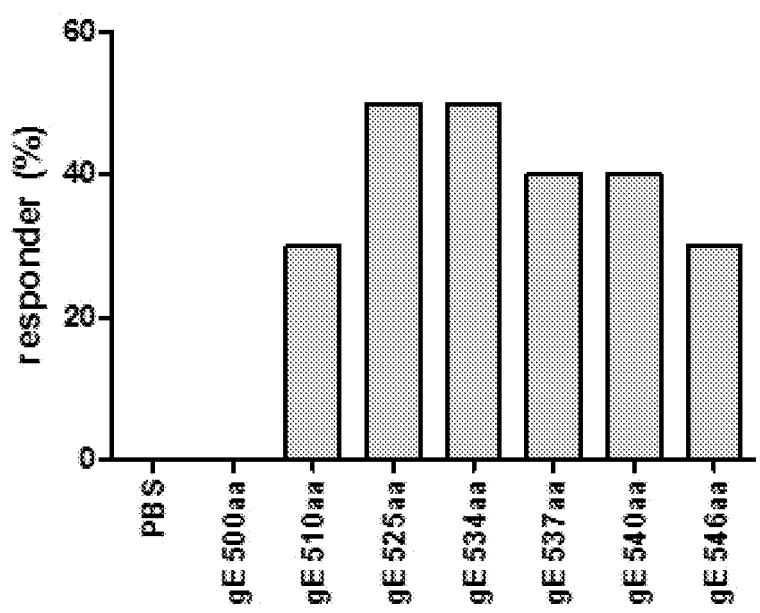
FIG. 8 illustrates results obtained by performing anti-gE specific IgG ELISA to compare humoral immune responses of gE fragments that are Varicella Zoster Virus antigens, and then summarizing the number of responders that show an antigen-specific antibody response.

After the antibody titer measurement, individuals with an OD value of 0.6 or higher were regarded as responders, and the results were summarized. As a result, there was no antigen-specific responder for gE 500 aa, and the number of responders after immunization with gE 510 aa was the same as that after immunization with gE 546 aa. The number of responders after immunization with gE 525 aa, gE 534 aa, gE 537 aa, or gE 540 aa was higher than the number of responders after immunization with gE 510 aa or gE 546 aa. That is, it was identified that gE 525 aa to gE 540 aa exhibited a higher number of responders (FIG. 8).

As a result, gE 534 aa to gE 543 aa showed higher values in the antibody titer measurement, and gE 525 aa to gE 540 aa showed higher values in antigen-specific responders. Therefore, in a case where the above two results are put together, it can be identified that gE 534 aa to 540 aa show higher immunogenicity.

INDUSTRIAL APPLICABILITY

The Varicella Zoster Virus surface protein (gE) antigen variant according to the present invention is a protein antigen. In a case of being used as a vaccine composition, the antigen variant exhibits excellent safety and high expression level in host cells as compared with a live virus vaccine. Thus, such an antigen variant is useful as a vaccine for preventing or treating Varicella Zoster Virus-induced varicella or herpes zoster.

As stated above, specific parts of the present invention have been described in detail. However, it is apparent to those skilled in the art that such specific description is only for illustrating preferred embodiments, and the scope of the present invention is not limited thereto. Accordingly, the substantial scope of the present invention will be defined by the appended claims and equivalents thereof.

SEQUENCE LISTING FREE TEXT

Attached electronic file.

The invention claimed is:

1. A vaccine composition comprising:
   (a) a variant of Varicella Zoster Virus (VZV) surface protein (gE) antigen, said VZV gE antigen comprising the base amino acid sequence of SEQ ID NO: 1 with the following mutations:
      1) a carboxy terminal truncation starting at any one of the amino acid residues of positions 534, 535, 536, 537, 538, or 540,
      2) wherein the amino acid residue at position 40 is threonine, and
      3) wherein the amino acid residue at position 536, if present, is leucine; and
   (b) an adjuvant.

2. The vaccine composition of claim 1, wherein the VZV gE antigen variant comprises the amino acid sequence of SEQ ID NO: 2, SEQ ID NO: 3, SEQ ID NO: 4, SEQ ID NO: 5, SEQ ID NO: 6, or SEQ ID NO: 8.

3. A recombinant vector comprising an exogenous gene encoding a variant of Varicella Zoster Virus (VZV) surface protein (gE) antigen,
   wherein the VZV gE antigen comprises the base amino acid sequence of SEQ ID NO: 1 with the following mutations;
      1) A carboxy terminal truncation starting at any one of the amino acid residues of positions 534, 535, 536, 537, 538, or 540,
      2) wherein the amino acid residue at position 40 is threonine; and
      3) wherein the amino acid residue at position 536, if present, is leucine; and
   wherein the exogenous gene being operably linked to a promoter.

4. The recombinant vector according to claim 3, wherein the gene comprises the nucleotide sequence of SEQ ID NO: 9, SEQ ID NO: 10, SEQ ID NO: 11, SEQ ID NO: 12, SEQ ID NO: 13, or SEQ ID NO: 15.

5. An isolated host cell transformed with the recombinant vector of claim 3.

6. An isolated host cell, transformed with the recombinant vector of claim 4.

7. A vaccine composition comprising as an active ingredient, the recombinant vector of claim 3.

8. A method for treating a subject infected with varicella or herpes zoster virus or inducing an immune response against varicella or herpes zoster virus in a subject, comprising:
   a step of administering, to the subject, an effective amount of the vaccine composition of claim 1.

9. A vaccine composition comprising as an active ingredient, the recombinant vector of claim 4.

10. A method for treating a subject infected with varicella or herpes zoster virus or inducing an immune response against varicella or herpes zoster virus in a subject, comprising:
    a step of administering, to the subject, an effective amount of the vaccine composition of claim 2.

11. A method for treating a subject infected with varicella or herpes zoster virus or inducing an immune response against varicella or herpes zoster virus in a subject, comprising:
    a step of administering, to the subject, an effective amount of the vaccine composition of claim 7.

12. A method for treating a subject infected with varicella or herpes zoster virus or inducing an immune response against varicella or herpes zoster virus in a subject, comprising:
    a step of administering, to the subject, an effective amount of the vaccine composition of claim 9.

* * * * *

SEQUENCE LISTING

```
<160> NUMBER OF SEQ ID NOS: 25

<210> SEQ ID NO 1
<211> LENGTH: 623
<212> TYPE: PRT
<213> ORGANISM: Artificial Sequence
<220> FEATURE:
<221> NAME/KEY: MISC_FEATURE
<222> LOCATION: (40)
<223> OTHER INFORMATION: Xaa is Thr or Ile
<220> FEATURE:
<221> NAME/KEY: MISC_FEATURE
<222> LOCATION: (536)
<223> OTHER INFORMATION: Xaa is Lue or Ile
<220> FEATURE:
<223> OTHER INFORMATION: Varicella Zoster Virus surface protein (gE)
      variant

<400> SEQUENCE: 1

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
                20                  25                  30

Leu Arg Tyr Asp Asp Phe His Xaa Asp Glu Asp Lys Leu Asp Thr Asn
            35                  40                  45

Ser Val Tyr Glu Pro Tyr Tyr His Ser Asp His Ala Glu Ser Ser Trp
        50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
```

```
            245                 250                 255
Glu Ala Asp Gln Pro Trp Ile Val Val Asn Thr Ser Thr Leu Phe Asp
            260                 265                 270
Glu Leu Glu Leu Asp Pro Pro Glu Ile Glu Pro Gly Val Leu Lys Val
            275                 280                 285
Leu Arg Thr Glu Lys Gln Tyr Leu Gly Val Tyr Ile Trp Asn Met Arg
        290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
                340                 345                 350
Val Gly Asp Thr Phe Ser Leu Ala Met His Leu Gln Tyr Lys Ile His
            355                 360                 365
Glu Ala Pro Phe Asp Leu Leu Leu Glu Trp Leu Tyr Val Pro Ile Asp
        370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
                420                 425                 430
Glu His Ala Asp Asn Tyr Thr Ala Tyr Cys Leu Gly Ile Ser His Met
            435                 440                 445
Glu Pro Ser Phe Gly Leu Ile Leu His Asp Gly Gly Thr Thr Leu Lys
        450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
                485                 490                 495
Val Asp His Phe Val Asn Ala Ile Glu Glu Arg Gly Phe Pro Pro Thr
            500                 505                 510
Ala Gly Gln Pro Pro Ala Thr Thr Lys Pro Lys Glu Ile Thr Pro Val
        515                 520                 525
Asn Pro Gly Thr Ser Pro Leu Xaa Arg Tyr Ala Ala Trp Thr Gly Gly
        530                 535                 540
Leu Ala Ala Val Val Leu Leu Cys Leu Val Ile Phe Leu Ile Cys Thr
545                 550                 555                 560
Ala Lys Arg Met Arg Val Lys Ala Tyr Arg Val Asp Lys Ser Pro Tyr
                565                 570                 575
Asn Gln Ser Met Tyr Tyr Ala Gly Leu Pro Val Asp Asp Phe Glu Asp
            580                 585                 590
Ser Glu Ser Thr Asp Thr Glu Glu Phe Gly Asn Ala Ile Gly Gly
            595                 600                 605
Ser His Gly Gly Ser Ser Tyr Thr Val Tyr Ile Asp Lys Thr Arg
            610                 615                 620

<210> SEQ ID NO 2
<211> LENGTH: 534
<212> TYPE: PRT
<213> ORGANISM: Artificial Sequence
<220> FEATURE:
<223> OTHER INFORMATION: Varicella Zoster Virus surface protein (gE)
      variant
```

<400> SEQUENCE: 2

```
Met Gly Thr Val Asn Lys Pro Val Gly Val Leu Met Gly Phe Gly
1               5                  10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
            35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
                115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
                195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
                260                 265                 270

Glu Leu Glu Leu Asp Pro Pro Glu Ile Glu Pro Gly Val Leu Lys Val
    275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
                340                 345                 350

Val Gly Asp Thr Phe Ser Leu Ala Met His Leu Gln Tyr Lys Ile His
            355                 360                 365

Glu Ala Pro Phe Asp Leu Leu Glu Trp Leu Tyr Val Pro Ile Asp
            370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
```

```
            405                 410                 415
Ser Pro His Leu Ala Gln Arg Val Ala Ser Thr Val Tyr Gln Asn Cys
        420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Thr Thr Leu Lys
        450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
            485                 490                 495

Val Asp His Phe Val Asn Ala Ile Glu Glu Arg Gly Phe Pro Pro Thr
        500                 505                 510

Ala Gly Gln Pro Pro Ala Thr Thr Lys Pro Lys Glu Ile Thr Pro Val
        515                 520                 525

Asn Pro Gly Thr Ser Pro
        530

<210> SEQ ID NO 3
<211> LENGTH: 535
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 3

Met Gly Thr Val Asn Lys Pro Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220
```

```
Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
            245                 250                 255

Glu Ala Asp Gln Pro Trp Ile Val Val Asn Thr Ser Thr Leu Phe Asp
        260                 265                 270

Glu Leu Glu Leu Asp Pro Pro Glu Ile Glu Pro Gly Val Leu Lys Val
    275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
            325                 330                 335

Arg Gly Ala Glu Phe His Met Trp Asn Tyr His Ser His Val Phe Ser
        340                 345                 350

Val Gly Asp Thr Phe Ser Leu Ala Met His Leu Gln Tyr Lys Ile His
    355                 360                 365

Glu Ala Pro Phe Asp Leu Leu Leu Glu Trp Leu Tyr Val Pro Ile Asp
370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
            405                 410                 415

Ser Pro His Leu Ala Gln Arg Val Ala Ser Thr Val Tyr Gln Asn Cys
        420                 425                 430

Glu His Ala Asp Asn Tyr Thr Ala Tyr Cys Leu Gly Ile Ser His Met
    435                 440                 445

Glu Pro Ser Phe Gly Leu Ile Leu His Asp Gly Gly Thr Thr Leu Lys
450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
            485                 490                 495

Val Asp His Phe Val Asn Ala Ile Glu Glu Arg Gly Phe Pro Pro Thr
        500                 505                 510

Ala Gly Gln Pro Pro Ala Thr Thr Lys Pro Lys Glu Ile Thr Pro Val
    515                 520                 525

Asn Pro Gly Thr Ser Pro Leu
530                 535
```

<210> SEQ ID NO 4
<211> LENGTH: 536
<212> TYPE: PRT
<213> ORGANISM: Artificial Sequence
<220> FEATURE:
<223> OTHER INFORMATION: Varicella Zoster Virus surface protein (gE) variant

<400> SEQUENCE: 4

```
Met Gly Thr Val Asn Lys Pro Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45
```

```
Ser Val Tyr Glu Pro Tyr Tyr His Ser Asp His Ala Glu Ser Ser Trp
 50                  55                  60

Val Asn Arg Gly Glu Ser Ser Arg Lys Ala Tyr Asp His Asn Ser Pro
 65                  70                  75                  80

Tyr Ile Trp Pro Arg Asn Asp Tyr Asp Gly Phe Leu Glu Asn Ala His
                 85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
            290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
            435                 440                 445

Glu Pro Ser Phe Gly Leu Ile Leu His Asp Gly Gly Thr Thr Leu Lys
450                 455                 460
```

-continued

```
Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Ser Thr
            485                 490                 495

Val Asp His Phe Val Asn Ala Ile Glu Glu Arg Gly Phe Pro Pro Thr
        500                 505                 510

Ala Gly Gln Pro Pro Ala Thr Thr Lys Pro Lys Glu Ile Thr Pro Val
        515                 520                 525

Asn Pro Gly Thr Ser Pro Leu Leu
    530                 535

<210> SEQ ID NO 5
<211> LENGTH: 537
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 5

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285
```

```
Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg
    530                 535

<210> SEQ ID NO 6
<211> LENGTH: 538
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 6

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
```

```
                100             105             110
Arg Leu Met Gln Pro Thr Gln Met Ser Ala Gln Glu Asp Leu Gly Asp
            115                 120                 125
Asp Thr Gly Ile His Val Ile Pro Thr Leu Asn Gly Asp Asp Arg His
        130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
            180                 185                 190
Gly Val Arg Tyr Thr Glu Thr Trp Ser Phe Leu Pro Ser Leu Thr Cys
        195                 200                 205
Thr Gly Asp Ala Ala Pro Ala Ile Gln His Ile Cys Leu Lys His Thr
    210                 215                 220
Thr Cys Phe Gln Asp Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                245                 250                 255
Glu Ala Asp Gln Pro Trp Ile Val Val Asn Thr Ser Thr Leu Phe Asp
            260                 265                 270
Glu Leu Glu Leu Asp Pro Pro Glu Ile Glu Pro Gly Val Leu Lys Val
        275                 280                 285
Leu Arg Thr Glu Lys Gln Tyr Leu Gly Val Tyr Ile Trp Asn Met Arg
    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
            340                 345                 350
Val Gly Asp Thr Phe Ser Leu Ala Met His Leu Gln Tyr Lys Ile His
        355                 360                 365
Glu Ala Pro Phe Asp Leu Leu Leu Glu Trp Leu Tyr Val Pro Ile Asp
    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
        435                 440                 445
Glu Pro Ser Phe Gly Leu Ile Leu His Asp Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Ser Thr
                485                 490                 495
Val Asp His Phe Val Asn Ala Ile Glu Glu Arg Gly Phe Pro Pro Thr
            500                 505                 510
Ala Gly Gln Pro Pro Ala Thr Thr Lys Pro Lys Glu Ile Thr Pro Val
        515                 520                 525
```

```
Asn Pro Gly Thr Ser Pro Leu Leu Arg Tyr
    530                 535

<210> SEQ ID NO 7
<211> LENGTH: 539
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 7

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
```

```
                340             345             350
Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
        370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala
    530                 535

<210> SEQ ID NO 8
<211> LENGTH: 540
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 8

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160
```

```
Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala
    530                 535                 540

<210> SEQ ID NO 9
<211> LENGTH: 1602
<212> TYPE: DNA
<213> ORGANISM: Artificial Sequence
<220> FEATURE:
<223> OTHER INFORMATION: Nucleic acid encodig Varicella Zoster Virus
``` surface protein (gE) variant

<400> SEQUENCE: 9

| atgggaacag tcaacaaacc agtcgtcggc gtgctgatgg gcttcggtat tattacagga | 60 |
| actctgagga ttactaaccc cgtgcgcgcc tctgtgctgc ggtacgacga tttccacaca | 120 |
| gacgaggata agctggacac caattccgtg tatgagccct actatcactc tgatcacgcc | 180 |
| gagagctcct gggtgaaccg ggcgagtct agcaggaagg cttacgacca caacagccct | 240 |
| tatatctggc cacggaatga ctacgatggc tttctggaga acgcccacga gcaccacggc | 300 |
| gtgtataatc agggcagagg catcgactct ggcgagcggc tgatgcagcc cacccagatg | 360 |
| agcgcccagg aggatctggg cgacgataca ggcatccacg tgatccctac cctgaatggc | 420 |
| gacgataggc acaagatcgt gaacgtggat cagagacagt acggcgacgt gttcaagggc | 480 |
| gatctgaatc ccaagcctca gggccagagg ctgatcgagg tgtccgtgga ggagaaccac | 540 |
| cccttcaccc tgagagcccc tatccagcgg atctacggcg tgaggtatac cgagacatgg | 600 |
| agctttctgc catccctgac atgcaccggc gacgctgctc ctgctatcca gcacatctgc | 660 |
| ctgaagcaca ccacatgttt tcaggacgtg gtggtggacg tggattgtgc cgagaataca | 720 |
| aaggaggatc agctggctga gatctcctac cggttccagg caagaaggga ggccgatcag | 780 |
| ccttggatcg tggtgaacac ctctacactg tttgacgagc tggagctgga tccccctgag | 840 |
| atcgagccag gcgtgctgaa ggtgctgaga accgagaagc agtacctggg cgtgtatatc | 900 |
| tggaacatgc ggggctctga cggcaccagc acatacgcta ccttcctggt cacatggaag | 960 |
| ggcgatgaga gacccggaa ccaacaccct gctgtgaccc ctcagccaag gggagctgag | 1020 |
| tttcacatgt ggaactatca ctcccacgtg ttctctgtgg gcgacaccct tagcctggcc | 1080 |
| atgcacctgc aatataagat ccacgaggct ccttttcgacc tgctgctgga gtggctgtat | 1140 |
| gtgcccatcg atcctacatg ccagccaatg aggctgtact ccacctgtct gtatcaccca | 1200 |
| aatgcccccc aatgcctgag ccacatgaac tccggctgta cctttacaag cccccacctg | 1260 |
| gcccagagag tggcttccac agtgtaccag aactgcgagc acgccgacaa ttacaccgct | 1320 |
| tattgtctgg gcatctctca catggagccc agcttcggcc tgatcctgca cgacggcggc | 1380 |
| accacactga gtttgtgga tacacccgag tccctgtctg gcctctacgt gttcgtggtg | 1440 |
| tacttcaacg gccacgtgga ggccgtggct tatacagtgg tgtctaccgt ggatcacttc | 1500 |
| gtgaacgcca tcgaggagag aggatttcca cctaccgctg gacagcctcc agctaccaca | 1560 |
| aagcctaagg aaatcacccc tgtcaatcct ggaacttcac ct | 1602 |

<210> SEQ ID NO 10
<211> LENGTH: 1605
<212> TYPE: DNA
<213> ORGANISM: Artificial Sequence
<220> FEATURE:
<223> OTHER INFORMATION: Nucleic acid encodig Varicella Zoster Virus
      surface protein (gE) variant

<400> SEQUENCE: 10

| atgggaacag tcaacaaacc agtcgtcggc gtgctgatgg gcttcggtat tattacagga | 60 |
| actctgagga ttactaaccc cgtgcgcgcc tctgtgctgc ggtacgacga tttccacaca | 120 |
| gacgaggata agctggacac caattccgtg tatgagccct actatcactc tgatcacgcc | 180 |
| gagagctcct gggtgaaccg ggcgagtct agcaggaagg cttacgacca caacagccct | 240 |
| tatatctggc cacggaatga ctacgatggc tttctggaga acgcccacga gcaccacggc | 300 |

| | |
|---|---|
| gtgtataatc agggcagagg catcgactct ggcgagcggc tgatgcagcc cacccagatg | 360 |
| agcgcccagg aggatctggg cgacgataca ggcatccacg tgatccctac cctgaatggc | 420 |
| gacgataggc acaagatcgt gaacgtggat cagagacagt acggcgacgt gttcaagggc | 480 |
| gatctgaatc ccaagcctca gggccagagg ctgatcgagg tgtccgtgga ggagaaccac | 540 |
| cccttcaccc tgagagcccc tatccagcgg atctacggcg tgaggtatac cgagacatgg | 600 |
| agctttctgc catccctgac atgcaccggc gacgctgctc ctgctatcca gcacatctgc | 660 |
| ctgaagcaca ccacatgttt tcaggacgtg gtggtggacg tggattgtgc cgagaataca | 720 |
| aaggaggatc agctggctga gatctcctac cggttccagg caagaaggag ggccgatcag | 780 |
| ccttggatcg tggtgaacac ctctacactg tttgacgagc tggagctgga tccccctgag | 840 |
| atcgagccag gcgtgctgaa ggtgctgaga accgagaagc agtacctggg cgtgtatatc | 900 |
| tggaacatgc ggggctctga cggcaccagc acatacgcta ccttcctggt cacatggaag | 960 |
| ggcgatgaga agacccggaa tccaacacct gctgtgaccc ctcagccaag gggagctgag | 1020 |
| tttcacatgt ggaactatca ctcccacgtg ttctctgtgg gcgacacctt tagcctggcc | 1080 |
| atgcacctgc aatataagat ccacgaggct cctttcgacc tgctgctgga gtggctgtat | 1140 |
| gtgcccatcg atcctacatg ccagccaatg aggctgtact ccacctgtct gtatcaccca | 1200 |
| aatgccccc aatgcctgag ccacatgaac tccggctgta cctttacaag cccccacctg | 1260 |
| gcccagagag tggcttccac agtgtaccag aactgcgagc acgccgacaa ttacaccgct | 1320 |
| tattgtctgg gcatctctca catggagccc agcttcggcc tgatcctgca cgacggcggc | 1380 |
| accacactga agtttgtgga tacacccgag tccctgtctg gcctctacgt gttcgtggtg | 1440 |
| tacttcaacg gccacgtgga ggccgtggct tatacagtgg tgtctaccgt ggatcacttc | 1500 |
| gtgaacgcca tcgaggagag aggatttcca cctaccgctg acagcctcc agctaccaca | 1560 |
| aagcctaagg aaatcacccc tgtcaatcct ggaacttcac tctg | 1605 |

<210> SEQ ID NO 11
<211> LENGTH: 1608
<212> TYPE: DNA
<213> ORGANISM: Artificial Sequence
<220> FEATURE:
<223> OTHER INFORMATION: Nucleic acid encodig Varicella Zoster Virus
    surface protein (gE) variant

<400> SEQUENCE: 11

| | |
|---|---|
| atgggaacag tcaacaaacc agtcgtcggc gtgctgatgg gcttcggtat tattacagga | 60 |
| actctgagga ttactaaccc cgtgcgcgcc tctgtgctgc ggtacgacga tttccacaca | 120 |
| gacgaggata gctggacac caattccgtg tatgagccct actatcactc tgatcacgcc | 180 |
| gagagctcct gggtgaaccg gggcgagtct agcaggaagg cttacgacca aacagccct | 240 |
| tatatctggc cacggaatga ctacgatggc tttctggaga acgcccacga gcaccacggc | 300 |
| gtgtataatc agggcagagg catcgactct ggcgagcggc tgatgcagcc cacccagatg | 360 |
| agcgcccagg aggatctggg cgacgataca ggcatccacg tgatccctac cctgaatggc | 420 |
| gacgataggc acaagatcgt gaacgtggat cagagacagt acggcgacgt gttcaagggc | 480 |
| gatctgaatc ccaagcctca gggccagagg ctgatcgagg tgtccgtgga ggagaaccac | 540 |
| cccttcaccc tgagagcccc tatccagcgg atctacggcg tgaggtatac cgagacatgg | 600 |
| agctttctgc catccctgac atgcaccggc gacgctgctc ctgctatcca gcacatctgc | 660 |
| ctgaagcaca ccacatgttt tcaggacgtg gtggtggacg tggattgtgc cgagaataca | 720 |

```
aaggaggatc agctggctga gatctcctac cggttccagg gcaagaagga ggccgatcag      780
ccttggatcg tggtgaacac ctctacactg tttgacgagc tggagctgga tcccctgag      840 atcgagccag gcgtgctgaa ggtgctgaga accgagaagc agtacctggg cgtgtatatc     900
tggaacatgc ggggctctga cggcaccagc acatacgcta ccttcctggt cacatggaag     960
ggcgatgaga agacccggaa tccaacacct gctgtgaccc ctcagccaag gggagctgag    1020
tttcacatgt ggaactatca ctcccacgtg ttctctgtgg cgacaccttt agcctggcc     1080 atgcacctgc aatataagat ccacgaggct ccttttcgacc tgctgctgga gtggctgtat   1140
gtgcccatcg atcctacatg ccagccaatg aggctgtact ccacctgtct gtatcaccca    1200
aatgcccccc aatgcctgag ccacatgaac tccggctgta cctttacaag ccccccacctg  1260 gcccagagag tggcttccac agtgtaccag aactgcgagc acgccgacaa ttacaccgct    1320
tattgtctgg gcatctctca catggagccc agcttcggcc tgatcctgca cgacggcggc    1380
accacactga gtttgtgga tacacccgag tccctgtctg gcctctacgt gttcgtggtg     1440
tacttcaacg gccacgtgga ggccgtggct tatacagtgg tgtctaccgt ggatcacttc    1500
gtgaacgcca tcgaggagag aggatttcca cctaccgctg acagcctcc agctaccaca    1560 aagcctaagg aaatcacccc tgtcaatcct ggaacttcac ctctgctg              1608
```

<210> SEQ ID NO 12
<211> LENGTH: 1611
<212> TYPE: DNA
<213> ORGANISM: Artificial Sequence
<220> FEATURE:
<223> OTHER INFORMATION: Nucleic acid encodig Varicella Zoster Virus
      surface protein (gE) variant

<400> SEQUENCE: 12

```
atgggaacag tcaacaaacc agtcgtcggc gtgctgatgg gcttcggtat tattacagga    60
actctgagga ttactaaccc cgtgcgcgcc tctgtgctgc ggtacgacga tttccacaca    120
gacgaggata agctggacac caattccgtg tatgagccct actatcactc tgatcacgcc    180
gagagctcct gggtgaaccg gggcgagtct agcaggaagg cttacgacca caacagccct    240
tatatctggc acggaatgcg ctacgatggc tttctggaga cgccacgga gcaccacggc     300 gtgtataatc agggcagagg catcgactct ggcgagcggc tgatgcagcc cacccagatg    360
agcgcccagg aggatctggg cgacgataca ggcatccacg tgatccctac cctgaatggc    420
gacgataggc acaagatcgt gaacgtggat cagagacagt acggcgacgt gttcaagggc    480
gatctgaatc ccaagcctca gggccagagg ctgatcgagg tgtccgtgga ggagaaccac    540
cccttcaccc tgagagcccc tatccagcgg atctacggcg tgaggtatac cgagacatgg    600
agctttctgc catccctgac atgcaccggc gacgctgctc ctgctatcca gcacatctgc    660
ctgaagcaca ccacatgttt tcaggacgtg gtggtggacg tggattgtgc cgagaataca    720
aaggaggatc agctggctga gatctcctac cggttccagg gcaagaagga ggccgatcag    780
ccttggatcg tggtgaacac ctctacactg tttgacgagc tggagctgga tcccctgag     840 atcgagccag gcgtgctgaa ggtgctgaga accgagaagc agtacctggg cgtgtatatc    900
tggaacatgc ggggctctga cggcaccagc acatacgcta ccttcctggt cacatggaag    960
ggcgatgaga agacccggaa tccaacacct gctgtgaccc ctcagccaag gggagctgag    1020
tttcacatgt ggaactatca ctcccacgtg ttctctgtgg cgacaccttt agcctggcc    1080 atgcacctgc aatataagat ccacgaggct ccttttcgacc tgctgctgga gtggctgtat  1140
```

```
gtgcccatcg atcctacatg ccagccaatg aggctgtact ccacctgtct gtatcaccca    1200 aatgccccc  aatgcctgag ccacatgaac tccggctgta cctttacaag cccccacctg    1260
gcccagagag tggcttccac agtgtaccag aactgcgagc acgccgacaa ttacaccgct    1320
tattgtctgg gcatctctca catggagccc agcttcggcc tgatcctgca cgacggcggc    1380
accacactga gtttgtgga  tacacccgag tccctgtctg gcctctacgt gttcgtggtg    1440
tacttcaacg ccacgtgga  ggccgtggct tatacagtgg tgtctaccgt ggatcacttc    1500
gtgaacgcca tcgaggagag aggatttcca cctaccgctg acagcctcc  agctaccaca    1560 aagcctaagg aaatcacccc tgtcaatcct ggaacttcac ctctgctgcg c             1611
```

<210> SEQ ID NO 13
<211> LENGTH: 1614
<212> TYPE: DNA
<213> ORGANISM: Artificial Sequence
<220> FEATURE:
<223> OTHER INFORMATION: Nucleic acid encodig Varicella Zoster Virus
      surface protein (gE) variant

<400> SEQUENCE: 13

```
atgggaacag tcaacaaacc agtcgtcggc gtgctgatgg gcttcggtat tattacagga     60
actctgagga ttactaaccc cgtgcgcgcc tctgtgctgc ggtacgacga tttccacaca    120
gacgaggata agctggacac caattccgtg tatgagccct actatcactc tgatcacgcc    180
gagagctcct gggtgaaccg ggcgagtct  agcaggaagg cttacgacca aacagccct     240 tatatctggc cacggaatga ctacgatggc tttctggaga cgccaccga  gcaccacggc    300 gtgtataatc agggcagagg catcgactct ggcgagcggc tgatgcagcc cacccagatg    360
agcgcccagg aggatctggg cgacgataca ggcatccacg tgatccctac cctgaatggc    420
gacgataggc acaagatcgt gaacgtggat cagagacagt acggcgacgt gttcaagggc    480
gatctgaatc ccaagcctca gggcagagg  ctgatcgagg tgtccgtgga ggagaaccac    540
cccttcaccc tgagagcccc tatccagcgg atctacggcg tgaggtatac cgagacatgg    600
agctttctgc catccctgac atgcaccggc gacgctgctc ctgctatcca gcacatctgc    660
ctgaagcaca ccacatgttt tcaggacgtg gtggtgacg  tggattgtgc cgagaatca    720 aaggaggatc agctggctga gatctcctac cggttccagg gcaagaagga ggccgatcag    780
ccttggatcg tggtgaacac ctctacactg tttgacgagc tggagctgga tcccctgag    840 atcgagccag gcgtgctgaa ggtgctgaga accgagaagc agtacctggg cgtgtatatc    900
tggaacatgc ggggctctga cggcaccagc acatacgcta ccttcctggt cacatggaag    960
ggcgatgaga agacccggaa tccaacacct gctgtgaccc ctcagccaag gggagctgag    1020
tttcacatgt ggaactatca ctcccacgtg ttctctgtgg cgacaccctt tagcctggcc    1080
atgcacctgc aatataagat ccacgaggct cctttcgacc tgctgctgga gtggctgtat    1140
gtgcccatcg atcctacatg ccagccaatg aggctgtact ccacctgtct gtatcaccca    1200 aatgccccc  aatgcctgag ccacatgaac tccggctgta cctttacaag cccccacctg    1260
gcccagagag tggcttccac agtgtaccag aactgcgagc acgccgacaa ttacaccgct    1320
tattgtctgg gcatctctca catggagccc agcttcggcc tgatcctgca cgacggcggc    1380
accacactga gtttgtgga  tacacccgag tccctgtctg gcctctacgt gttcgtggtg    1440
tacttcaacg ccacgtgga  ggccgtggct tatacagtgg tgtctaccgt ggatcacttc    1500
gtgaacgcca tcgaggagag aggatttcca cctaccgctg acagcctcc  agctaccaca    1560
```
aagcctaagg aaatcacccc tgtcaatcct ggaacttcac ctctgctgcg ctac        1614

<210> SEQ ID NO 14
<211> LENGTH: 1617
<212> TYPE: DNA
<213> ORGANISM: Artificial Sequence
<220> FEATURE:
<223> OTHER INFORMATION: Nucleic acid encodig Varicella Zoster Virus
      surface protein (gE) variant

<400> SEQUENCE: 14
atgggaacag tcaacaaacc agtcgtcggc gtgctgatgg gcttcggtat tattacagga      60
actctgagga ttactaaccc cgtgcgcgcc tctgtgctgc ggtacgacga tttccacaca     120
gacgaggata agctggacac caattccgtg tatgagccct actatcactc tgatcacgcc     180
gagagctcct gggtgaaccg gggcgagtct agcaggaagg cttacgacca caacagccct     240
tatatctggc cacggaatga ctacgatggc tttctggaga cgcccacga gcaccacggc     300 gtgtataatc agggcagagg catcgactct ggcgagcggc tgatgcagcc cacccagatg     360
agcgcccagg aggatctggg cgacgataca ggcatccacg tgatccctac cctgaatggc     420
gacgataggc acaagatcgt gaacgtggat cagagacagt acggcgacgt gttcaagggc     480
gatctgaatc ccaagcctca gggccagagg ctgatcgagg tgtccgtgga ggagaaccac     540
cccttcaccc tgagagcccc tatccagcgg atctacggcg tgaggtatac cgagacatgg     600
agctttctgc catccctgac atgcaccggc gacgctgctc ctgctatcca gcacatctgc     660
ctgaagcaca ccacatgttt tcaggacgtg gtggtggacg tggattgtgc cgagaataca     720
aaggaggatc agctggctga gatctcctac cggttccagg caagaaggga ggccgatcag     780
ccttggatcg tggtgaacac ctctacactg tttgacgagc tggagctgga tccccctgag     840
atcgagccag gcgtgctgaa ggtgctgaga accgagaagc agtacctggg cgtgtatatc     900
tggaacatgc ggggctctga cggcaccagc acatacgcta ccttcctggt cacatggaag     960
ggcgatgaga agacccggaa tccaacacct gctgtgaccc ctcagccaag gggagctgag    1020
tttcacatgt ggaactatca ctcccacgtg ttctctgtgg gcgacacctt tagcctggcc    1080
atgcacctgc aatataagat ccacgaggct cctttcgacc tgctgctgga gtggctgtat    1140
gtgcccatcg atcctacatg ccagccaatg aggctgtact ccacctgtct gtatcaccca    1200 aatgccccc aatgcctgag ccacatgaac tccggctgta cctttacaag ccccacctg     1260 gcccagagag tggcttccac agtgtaccag aactgcgagc acgccgacaa ttacaccgct    1320
tattgtctgg gcatctctca catggagccc agcttcggcc tgatcctgca cgacggcggc    1380
accacactga gtttgtgga tacacccgag tccctgtctg cctctacgt gttcgtggtg     1440 tacttcaacg gccacgtgga ggccgtggct tatacagtgg tgtctaccgt ggatcacttc    1500
gtgaacgcca tcgaggagag aggatttcca cctaccgctg acagcctcc agctaccaca    1560 aagcctaagg aaatcacccc tgtcaatcct ggaacttcac ctctgctgcg ctacgca      1617

<210> SEQ ID NO 15
<211> LENGTH: 1620
<212> TYPE: DNA
<213> ORGANISM: Artificial Sequence
<220> FEATURE:
<223> OTHER INFORMATION: Nucleic acid encodig Varicella Zoster Virus
      surface protein (gE) variant

<400> SEQUENCE: 15
atgggaacag tcaacaaacc agtcgtcggc gtgctgatgg gcttcggtat tattacagga      60

```
actctgagga ttactaaccc cgtgcgcgcc tctgtgctgc ggtacgacga tttccacaca    120
gacgaggata agctggacac caattccgtg tatgagccct actatcactc tgatcacgcc    180
gagagctcct gggtgaaccg gggcgagtct agcaggaagg cttacgacca acagccct     240
tatatctggc cacggaatga ctacgatggc tttctggaga cgcccacga gcaccacggc    300
gtgtataatc agggcagagg catcgactct ggcgagcggc tgatgcagcc cacccagatg   360
agcgcccagg aggatctggg cgacgataca ggcatccacg tgatccctac cctgaatggc   420
gacgataggc acaagatcgt gaacgtggat cagagacagt acggcgacgt gttcaagggc   480
gatctgaatc ccaagcctca gggccagagg ctgatcgagg tgtccgtgga ggagaaccac   540
cccttcaccc tgagagcccc tatccagcgg atctacggcg tgaggtatac cgagacatgg   600
agctttctgc catccctgac atgcaccggc gacgctgctc ctgctatcca gcacatctgc   660
ctgaagcaca ccacatgttt tcaggacgtg gtggtggacg tggattgtgc cgagaataca   720
aaggaggatc agctggctga gatctcctac cggttccagg caagaaggga ggccgatcag   780
ccttggatcg tggtgaacac ctctacactg tttgacgagc tggagctgga tccccctgag   840
atcgagccag cgtgctgaa ggtgctgaga accgagaagc agtacctggg cgtgtatatc    900
tggaacatgc ggggctctga cggcaccagc acatacgcta ccttcctggt cacatggaag   960
ggcgatgaga gacccggaa tccaacacct gctgtgaccc ctcagccaag ggagctgag   1020
tttcacatgt ggaactatca ctcccacgtg ttctctgtgg gcgacacctt tagcctggcc   1080
atgcacctgc aatataagat ccacgaggct cctttcgacc tgctgctgga gtggctgtat   1140
gtgcccatcg atcctacatg ccagccaatg aggctgtact ccacctgtct gtatcaccca   1200
aatgcccccc aatgcctgag ccacatgaac tccggctgta cctttacaag ccccacctg   1260
gcccagagag tggcttccac agtgtaccag aactgcgagc acgccgacaa ttacaccgct   1320
tattgtctgg gcatctctca catggagccc agcttcggcc tgatcctgca cgacggcggc   1380
accacactga agtttgtgga tacacccgag tccctgtctg gcctctacgt gttcgtggtg   1440
tacttcaacg ccacgtgga ggccgtggct atacagtgg tgtctaccgt ggatcacttc    1500
gtgaacgcca tcgaggagag aggattccca cctaccgctg gacagcctcc agctaccaca   1560
aagcctaagg aaaatcacccc tgtcaatcct ggaacttcac ctctgctgcg ctacgcagcc   1620
```

<210> SEQ ID NO 16
<211> LENGTH: 500
<212> TYPE: PRT
<213> ORGANISM: Artificial Sequence
<220> FEATURE:
<223> OTHER INFORMATION: Varicella Zoster Virus surface protein (gE) variant

<400> SEQUENCE: 16

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80
```

```
Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe
```

-continued

```
               500

<210> SEQ ID NO 17
<211> LENGTH: 505
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 17

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350
```

-continued

```
Val Gly Asp Thr Phe Ser Leu Ala Met His Leu Gln Tyr Lys Ile His
            355                 360                 365
Glu Ala Pro Phe Asp Leu Leu Leu Glu Trp Leu Tyr Val Pro Ile Asp
        370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
        435                 440                 445
Glu Pro Ser Phe Gly Leu Ile Leu His Asp Gly Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
                485                 490                 495
Val Asp His Phe Val Asn Ala Ile Glu
            500                 505

<210> SEQ ID NO 18
<211> LENGTH: 510
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 18

Met Gly Thr Val Asn Lys Pro Val Val Gly Val Leu Met Gly Phe Gly
1               5                   10                  15
Ile Ile Thr Gly Thr Leu Arg Ile Thr Asn Pro Val Arg Ala Ser Val
            20                  25                  30
Leu Arg Tyr Asp Asp Phe His Thr Asp Glu Asp Lys Leu Asp Thr Asn
        35                  40                  45
Ser Val Tyr Glu Pro Tyr Tyr His Ser Asp His Ala Glu Ser Ser Trp
    50                  55                  60
Val Asn Arg Gly Glu Ser Ser Arg Lys Ala Tyr Asp His Asn Ser Pro
65                  70                  75                  80
Tyr Ile Trp Pro Arg Asn Asp Tyr Asp Gly Phe Leu Glu Asn Ala His
                85                  90                  95
Glu His His Gly Val Tyr Asn Gln Gly Arg Gly Ile Asp Ser Gly Glu
            100                 105                 110
Arg Leu Met Gln Pro Thr Gln Met Ser Ala Gln Glu Asp Leu Gly Asp
        115                 120                 125
Asp Thr Gly Ile His Val Ile Pro Thr Leu Asn Gly Asp Asp Arg His
    130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
            180                 185                 190
Gly Val Arg Tyr Thr Glu Thr Trp Ser Phe Leu Pro Ser Leu Thr Cys
        195                 200                 205
```

```
Thr Gly Asp Ala Ala Pro Ala Ile Gln His Ile Cys Leu Lys His Thr
            210                 215                 220
Thr Cys Phe Gln Asp Val Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                245                 250                 255
Glu Ala Asp Gln Pro Trp Ile Val Val Asn Thr Ser Thr Leu Phe Asp
            260                 265                 270
Glu Leu Glu Leu Asp Pro Pro Glu Ile Glu Pro Gly Val Leu Lys Val
        275                 280                 285
Leu Arg Thr Glu Lys Gln Tyr Leu Gly Val Tyr Ile Trp Asn Met Arg
    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
            340                 345                 350
Val Gly Asp Thr Phe Ser Leu Ala Met His Leu Gln Tyr Lys Ile His
        355                 360                 365
Glu Ala Pro Phe Asp Leu Leu Leu Glu Trp Leu Tyr Val Pro Ile Asp
    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
        435                 440                 445
Glu Pro Ser Phe Gly Leu Ile Leu His Asp Gly Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
                485                 490                 495
Val Asp His Phe Val Asn Ala Ile Glu Glu Arg Gly Phe Pro
            500                 505                 510

<210> SEQ ID NO 19
<211> LENGTH: 515
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 19

Met Gly Thr Val Asn Lys Pro Val Val Gly Val Leu Met Gly Phe Gly
1               5                   10                  15
Ile Ile Thr Gly Thr Leu Arg Ile Thr Asn Pro Val Arg Ala Ser Val
                20                  25                  30
Leu Arg Tyr Asp Asp Phe His Thr Asp Glu Asp Lys Leu Asp Thr Asn
            35                  40                  45
Ser Val Tyr Glu Pro Tyr Tyr His Ser Asp His Ala Glu Ser Ser Trp
```

```
            50                  55                  60
Val Asn Arg Gly Glu Ser Ser Arg Lys Ala Tyr Asp His Asn Ser Pro
 65                  70                  75                  80

Tyr Ile Trp Pro Arg Asn Asp Tyr Asp Gly Phe Leu Glu Asn Ala His
                     85                  90                  95

Glu His His Gly Val Tyr Asn Gln Arg Gly Ile Asp Ser Gly Glu
                100                 105                 110

Arg Leu Met Gln Pro Thr Gln Met Ser Ala Gln Glu Asp Leu Gly Asp
                115                 120                 125

Asp Thr Gly Ile His Val Ile Pro Thr Leu Asn Gly Asp Asp Arg His
                130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
                195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
                260                 265                 270

Glu Leu Glu Leu Asp Pro Pro Glu Ile Glu Pro Gly Val Leu Lys Val
                275                 280                 285

Leu Arg Thr Glu Lys Gln Tyr Leu Gly Val Tyr Ile Trp Asn Met Arg
                290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser Val Phe Ser
                340                 345                 350

Val Gly Asp Thr Phe Ser Leu Ala Met His Leu Gln Tyr Lys Ile His
                355                 360                 365

Glu Ala Pro Phe Asp Leu Leu Leu Glu Trp Leu Tyr Val Pro Ile Asp
                370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
                420                 425                 430

Glu His Ala Asp Asn Tyr Thr Ala Tyr Cys Leu Gly Ile Ser His Met
                435                 440                 445

Glu Pro Ser Phe Gly Leu Ile Leu His Asp Gly Thr Thr Leu Lys
                450                 455                 460

Phe Val Asp Thr Pro Glu Ser Leu Ser Gly Leu Tyr Val Phe Val Val
465                 470                 475                 480
```

```
Tyr Phe Asn Gly His Val Glu Ala Val Ala Tyr Thr Val Val Ser Thr
                485                 490                 495

Val Asp His Phe Val Asn Ala Ile Glu Arg Gly Phe Pro Pro Thr
            500                 505                 510

Ala Gly Gln
        515

<210> SEQ ID NO 20
<211> LENGTH: 520
<212> TYPE: PRT
<213> ORGANISM: Artificial Sequence
<220> FEATURE:
<223> OTHER INFORMATION: Varicella Zoster Virus surface protein (g

```
            305                 310                 315                 320
Gly Asp Glu Lys Thr Arg Asn Pro Thr Pro Ala Val Thr Pro Gln Pro
                    325                 330                 335

Arg Gly Ala Glu Phe His Met Trp Asn Tyr His Ser His Val Phe Ser
                340                 345                 350

Val Gly Asp Thr Phe Ser Leu Ala Met His Leu Gln Tyr Lys Ile His
            355                 360                 365

Glu Ala Pro Phe Asp Leu Leu Leu Gly Trp Leu Tyr Val Pro Ile Asp
        370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
                420                 425                 430

Glu His Ala Asp Asn Tyr Thr Ala Tyr Cys Leu Gly Ile Ser His Met
            435                 440                 445

Glu Pro Ser Phe Gly Leu Ile Leu His Asp Gly Gly Thr Thr Leu Lys
        450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr
        515                 520

<210> SEQ ID NO 21
<211> LENGTH: 525
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 21

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140
```

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
            165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
            245                 250                 255

Glu Ala Asp Gln Pro Trp Ile Val Val Asn Thr Ser Thr Leu Phe Asp
        260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
            325                 330                 335

Arg Gly Ala Glu Phe His Met Trp Asn Tyr His Ser His Val Phe Ser
        340                 345                 350

Val Gly Asp Thr Phe Ser Leu Ala Met His Leu Gln Tyr Lys Ile His
    355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
            405                 410                 415

Ser Pro His Leu Ala Gln Arg Val Ala Ser Thr Val Tyr Gln Asn Cys
        420                 425                 430

Glu His Ala Asp Asn Tyr Thr Ala Tyr Cys Leu Gly Ile Ser His Met
    435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
            485                 490                 495

Val Asp His Phe Val Asn Ala Ile Glu Glu Arg Gly Phe Pro Pro Thr
        500                 505                 510

Ala Gly Gln Pro Pro Ala Thr Thr Lys Pro Lys Glu Ile
        515                 520                 525

<210> SEQ ID NO 22
<211> LENGTH: 530
<212> TYPE: PRT
<213> ORGANISM: Artificial Sequence
<220> FEATURE:
<223> OTHER INFORMATION: Varicella Zoster Virus surface protein (gE)

variant

<400> SEQUENCE: 22

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400
```

-continued

```
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
        435                 440                 445
Glu Pro Ser Phe Gly Leu Ile Leu His Asp Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Ser Thr
                485                 490                 495
Val Asp His Phe Val Asn Ala Ile Glu Glu Arg Gly Phe Pro Pro Thr
                500                 505                 510
Ala Gly Gln Pro Pro Ala Thr Thr Lys Pro Lys Glu Ile Thr Pro Val
            515                 520                 525
Asn Pro
    530

<210> SEQ ID NO 23
<211> LENGTH: 543
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 23

Met Gly Thr Val Asn Lys Pro Val Val Gly Val Leu Met Gly Phe Gly
1               5                   10                  15
Ile Ile Thr Gly Thr Leu Arg Ile Thr Asn Pro Val Arg Ala Ser Val
                20                  25                  30
Leu Arg Tyr Asp Asp Phe His Thr Asp Glu Asp Lys Leu Asp Thr Asn
            35                  40                  45
Ser Val Tyr Glu Pro Tyr Tyr His Ser Asp His Ala Glu Ser Ser Trp
    50                  55                  60
Val Asn Arg Gly Glu Ser Ser Arg Lys Ala Tyr Asp His Asn Ser Pro
65                  70                  75                  80
Tyr Ile Trp Pro Arg Asn Asp Tyr Asp Gly Phe Leu Glu Asn Ala His
                85                  90                  95
Glu His His Gly Val Tyr Asn Gln Gly Arg Gly Ile Asp Ser Gly Glu
            100                 105                 110
Arg Leu Met Gln Pro Thr Gln Met Ser Ala Gln Glu Asp Leu Gly Asp
        115                 120                 125
Asp Thr Gly Ile His Val Ile Pro Thr Leu Asn Gly Asp Asp Arg His
    130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
            180                 185                 190
Gly Val Arg Tyr Thr Glu Thr Trp Ser Phe Leu Pro Ser Leu Thr Cys
        195                 200                 205
Thr Gly Asp Ala Ala Pro Ala Ile Gln His Ile Cys Leu Lys His Thr
    210                 215                 220
```

-continued

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
            245                 250                 255

Glu Ala Asp Gln Pro Trp Ile Val Val Asn Thr Ser Thr Leu Phe Asp
        260                 265                 270

Glu Leu Glu Leu Asp Pro Pro Glu Ile Glu Pro Gly Val Leu Lys Val
    275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly
    530                 535                 540

<210> SEQ ID NO 24
<211> LENGTH: 546
<212> TYPE: PRT
<213> ORGANISM: Artificial Sequence
<220> FEATURE:
<223> OTHER INFORMATION: Varicella Zoster Virus surface protein (gE)
      variant

<400> SEQUENCE: 24

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn

```
             35                  40                  45
Ser Val Tyr Glu Pro Tyr Tyr His Ser Asp His Ala Glu Ser Ser Trp
 50                  55                  60
Val Asn Arg Gly Glu Ser Ser Arg Lys Ala Tyr Asp His Asn Ser Pro
 65                  70                  75                  80
Tyr Ile Trp Pro Arg Asn Asp Tyr Asp Gly Phe Leu Glu Asn Ala His
                     85                  90                  95
Glu His His Gly Val Tyr Asn Gln Gly Arg Gly Ile Asp Ser Gly Glu
                    100                 105                 110
Arg Leu Met Gln Pro Thr Gln Met Ser Ala Gln Glu Asp Leu Gly Asp
                    115                 120                 125
Asp Thr Gly Ile His Val Ile Pro Thr Leu Asn Gly Asp Asp Arg His
                    130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                    165                 170                 175
Glu Glu Asn His Pro Phe Thr Leu Arg Ala Pro Ile Gln Arg Ile Tyr
                    180                 185                 190
Gly Val Arg Tyr Thr Glu Thr Trp Ser Phe Leu Pro Ser Leu Thr Cys
                    195                 200                 205
Thr Gly Asp Ala Ala Pro Ala Ile Gln His Ile Cys Leu Lys His Thr
                    210                 215                 220
Thr Cys Phe Gln Asp Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                    245                 250                 255
Glu Ala Asp Gln Pro Trp Ile Val Val Asn Thr Ser Thr Leu Phe Asp
                    260                 265                 270
Glu Leu Glu Leu Asp Pro Pro Glu Ile Glu Pro Gly Val Leu Lys Val
                    275                 280                 285
Leu Arg Thr Glu Lys Gln Tyr Leu Gly Val Tyr Ile Trp Asn Met Arg
                    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                    325                 330                 335
Arg Gly Ala Glu Phe His Met Trp Asn Tyr His Ser His Val Phe Ser
                    340                 345                 350
Val Gly Asp Thr Phe Ser Leu Ala Met His Leu Gln Tyr Lys Ile His
                    355                 360                 365
Glu Ala Pro Phe Asp Leu Leu Leu Glu Trp Leu Tyr Val Pro Ile Asp
                    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                    405                 410                 415
Ser Pro His Leu Ala Gln Arg Val Ala Ser Thr Val Tyr Gln Asn Cys
                    420                 425                 430
Glu His Ala Asp Asn Tyr Thr Ala Tyr Cys Leu Gly Ile Ser His Met
                    435                 440                 445
Glu Pro Ser Phe Gly Leu Ile Leu His Asp Gly Gly Thr Thr Leu Lys
                    450                 455                 460
```

```
Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala
545

<210> SEQ ID NO 25
<211> LENGTH: 9
<212> TYPE: PRT
<213> ORGANISM: Artificial Sequence
<220> FEATURE:
<223> OTHER INFORMATION: C-terminal fragment of Varicella Zoster Virus
      surface protein(gE)

<400> SEQUENCE: 25

Tyr Ala Ala Trp Thr Gly Gly Leu Ala
1               5
```